United States Patent
Dong

(10) Patent No.: US 8,999,940 B2
(45) Date of Patent: Apr. 7, 2015

(54) ANALOGUES OF GLUCOSE-DEPENDENT INSULINOTROPIC POLYPEPTIDE (GIP) MODIFIED AT N-TERMINAL

(75) Inventor: Zheng Xin Dong, Holliston, MA (US)

(73) Assignee: Ipsen Pharma S.A.S., Boulogne-Billancourt (FR)

( * ) Notice: Subject to any disclaimer, the term of this patent is extended or adjusted under 35 U.S.C. 154(b) by 979 days.

(21) Appl. No.: 13/057,966

(22) PCT Filed: Aug. 7, 2009

(86) PCT No.: PCT/US2009/004559
§ 371 (c)(1),
(2), (4) Date: Feb. 12, 2011

(87) PCT Pub. No.: WO2010/016944
PCT Pub. Date: Feb. 11, 2010

(65) Prior Publication Data
US 2011/0136725 A1      Jun. 9, 2011

Related U.S. Application Data

(60) Provisional application No. 61/188,187, filed on Aug. 7, 2008, provisional application No. 61/200,612, filed on Dec. 2, 2008.

(51) Int. Cl.
  *A61K 38/16*  (2006.01)
  *C07K 14/00*  (2006.01)
  *A61P 3/10*  (2006.01)
  *A61P 3/06*  (2006.01)
  *C07K 14/605*  (2006.01)
  *A61K 38/00*  (2006.01)

(52) U.S. Cl.
  CPC ............... *C07K 14/605* (2013.01); *A61K 38/00* (2013.01)

(58) Field of Classification Search
  None
  See application file for complete search history.

(56) References Cited

U.S. PATENT DOCUMENTS

| | | | |
|---|---|---|---|
| 4,562,175 A | | 12/1985 | Chang et al. |
| 6,921,748 B1 * | | 7/2005 | O'Harte et al. ............... 514/5.9 |
| 7,091,183 B1 | | 8/2006 | Wolfe et al. |
| 2005/0277590 A1 * | | 12/2005 | O'Harte et al. ............... 514/12 |
| 2007/0042952 A1 | | 2/2007 | Dong et al. |
| 2008/0009603 A1 | | 1/2008 | Gault et al. |
| 2008/0124347 A1 | | 5/2008 | Kim et al. |

FOREIGN PATENT DOCUMENTS

| | | |
|---|---|---|
| EP | 1359159 A2 | 11/2003 |
| EP | 1942115 A1 | 7/2008 |
| WO | 03/082898 A2 | 10/2003 |
| WO | 2004/037195 | 5/2004 |
| WO | 2005/082928 A2 | 9/2005 |
| WO | 2006/086769 | 8/2006 |
| WO | 2006/121904 A1 | 11/2006 |
| WO | WO 2007/028632 | 3/2007 |
| WO | WO-2007/028633 * | 3/2007 |
| WO | WO 2007/028633 | 3/2007 |

OTHER PUBLICATIONS

Green, Brian D. "Structurally Modified Analogues of Glucagon-Like Peptide-1 (GLP-1) and Glucose-Dependent Insulinotropic Polypeptide (GIP) As Future Antidiabetic Agents," Current Pharmaceutical Design, 2004, p. 3651-3662, vol. 10, No. 29.

O'Harte, Finbarr P.M. et al. "Antagonistic effects of two novel GIP analogs, (Hyp3)GIP and (Hyp3) GIPLys16PAL, on the biological actions of GIP and longer-term effects in diabetic ob/ob mice," American Journal of Physiology-Endocrinology and Metabolism, 2007, E1674-E1682, vol. 292, No. 6.

Irwin, Nigel et al. "Degradation, Insulin Secretion, and Antihyperglycemic Actions of Two Palmitate-Derivitized N-Terminal Pyroglutamyl Analogues of Glucose-Dependent Insulinotropic Polypeptide," Journal of Medicinal Chemstry, 2005, p. 1244-1250, vol. 48, No. 4.

Irwin, Nigel et al. "Evaluation of the antidiabetic activity of DPP IV resistant N-terminally modified versus mid-chain acylated analogues of glucose-dependent insulinotropic polypeptide," Biochemical Pharmacology, 2006, p. 719-728, vol. 72, No. 6.

* cited by examiner

*Primary Examiner* — Satyanarayana R Gudibande
(74) *Attorney, Agent, or Firm* — Janice M. Klunder; Eileen J. Ennis

(57) ABSTRACT

There is provided a novel series of analogues of glucose-dependent insulinotropic polypeptide compounds, pharmaceutical compositions containing said compounds, and the use of said compounds as GIP-receptor agonists or antagonists for treatment of GIP-receptor mediated conditions, such as non-insulin dependent diabetes mellitus and obesity.

18 Claims, No Drawings

ANALOGUES OF GLUCOSE-DEPENDENT INSULINOTROPIC POLYPEPTIDE (GIP) MODIFIED AT N-TERMINAL

This application is a United States national stage filing under 35 U.S.C. §371 of international (PCT) application no. PCT/US2009/004559, filed Aug. 7, 2009, and designating the US, which claims priority to U.S. provisional application Nos. 61/188,187, filed Aug. 7, 2008, and 61/200,612, filed Dec. 2, 2008.

FIELD OF THE INVENTION

The present invention relates to the area of novel analogues of glucose-dependent insulinotropic polypeptide compounds, pharmaceutical compositions containing said compounds, and the use of said compounds as GIP-receptor agonists or antagonists for treatment of GIP-receptor mediated conditions, such as non-insulin dependent diabetes mellitus and obesity.

BACKGROUND ART

Glucose-dependent insulinotropic polypeptide ("GIP", also known as "gastric inhibitory polypeptide"; SEQ ID NO:1) is a 42-residue peptide secreted by enteroendorine K-cells of the small intestine into the bloodstream in response to oral nutrient ingestion. GIP inhibits the secretion of gastric acid, and it has been shown to be a potent stimulant for the secretion of insulin from pancreatic beta cells after oral glucose ingestion (the "incretin effect") (Creutzfeldt, W., et al., 1979, *Diabetologia*, 16:75-85).

Insulin release induced by the ingestion of glucose and other nutrients is due to both hormonal and neural factors (Creutzfeldt, W., et al., 1985, *Diabetologia*, 28:565-573). Several gastrointestinal regulatory peptides have been proposed as incretins, and among these candidates, only GIP and glucagon-like peptide 1 ("GLP-1") appear to fulfill the requirements to be considered physiological stimulants of postprandial insulin release (Nauck, et al., 1989, *J. Clin. Endorinol. Metab.*, 69:654-662). It has been shown that the combined effects of GIP and GLP-1 are sufficient to explain the full incretin effect of the enteroinsular axis (Fehmann, H. C., et al., 1989, *FEBS Lett.*, 252:109-112).

As is well known to those skilled in the art, the known and potential uses of GIP are varied and multitudinous. Thus, the administration of the compounds of this invention for purposes of eliciting an agonist effect can have the same effects and uses as GIP itself. These varied uses of GIP may be summarized as follows: treating a disease selected from the group consisting of type 1 diabetes, type 2 diabetes (Visboll, T., 2004, *Dan. Med. Bull.*, 51:364-70), insulin resistance (WO 2005/082928), obesity (Green, B. D., et al., 2004, *Current Pharmaceutical Design*, 10:3651-3662), metabolic disorder (Gault, V. A., et al., 2003, *Biochem. Biophys. Res. Commun.*, 308:207-213), central nervous system disease, neurodegenerative disease, congestive heart failure, hypoglycemia, and disorders wherein the reduction of food intake and weight loss are desired. In pancreatic islets, GIP not only enhances insulin secretion acutely, but it also stimulates insulin production through enhancement of proinsulin transcription and translation (Wang, et al., 1996, *Mol. Cell. Endocrinol.*, 116: 81-87) and enhances the growth and survival of pancreatic beta cells (Trumper, et al., 2003, *Diabetes*, 52:741-750). In addition to effects on the pancreas to enhance insulin secretion, GIP also has effects on insulin target tissues directly to lower plasma glucose: enhancement of glucose uptake in adipose (Eckel, et al., 1979, *Diabetes*, 28:1141-1142) and muscle (O'Harte, et al., 1998, *J. Endocrinol.*, 156:237-243), and inhibition of hepatic glucose production (Elahi, D., et al., 1986, *Can. J. Physiol. Pharmacol.*, 65:A18).

In addition, a GIP receptor antagonist in accordance with the present invention inhibits, blocks or reduces glucose absorption from the intestine of an animal. In accordance with this observation, therapeutic compositions containing GIP antagonists may be used in patients with non-insulin dependent diabetes mellitus to improve tolerance to oral glucose in mammals, such as humans, to prevent, inhibit or reduce obesity by inhibiting, blocking or reducing glucose absorption from the intestine of the mammal.

The use of unmodified GIP as a therapeutic, however, is limited by the short in vivo half-life of about 2 minutes (Said and Mutt, 1970, *Science*, 169:1217-1218). In serum, both incretins, GIP and GLP-1, are degraded by dipeptidyl peptidase IV ("DPPIV"). Improving the stability of GIP to proteolysis not only maintains the activity of GIP at its receptor but, more importantly, prevents the production of GIP fragments, some of which act as GIP receptor antagonists (Gault, et al., 2002, *J. Endocrinol.*, 175:525-533). Reported modifications have included protection of the N-terminus of GIP from proteolysis by DPPIV through modification of the N-terminal tyrosine (O'Harte, et al., 2002, *Diabetologia*, 45:1281-1291), mutation of the alanine at position 2 (Hinke, et al., 2002, *Diabetes*, 51:656-661), mutation of glutamic acid at position 3 (Gault, et al., 2003, *Biochem. Biophys. Res. Commun.*, 308:207-213), and mutation of alanine at position 13 (Gault, et al., 2003, *Cell Biol. International*, 27:41-46), The following patent applications have been filed related to the effects of GIP analogues on the function of various target organs and their potential use as therapeutic agents:

PCT publication WO 00/58360 discloses peptidyl analogues of GIP which stimulate the release of insulin. In particular, this application discloses specific peptidyl analogues comprising at least 15 amino acid residues from the N-terminal end of GIP(1-42), e.g., an analogue of GIP containing exactly one amino acid substitution or modification at positions 1, 2 and 3, such as [Pro$^3$](1-42).

PCT publication WO 98/24464 discloses an antagonist of GIP consisting essentially of a 24-amino acid polypeptide corresponding to positions 7-30 of the sequence of GIP, a method of treating non-insulin dependent diabetes mellitus and a method of improving glucose tolerance in a non-insulin dependent diabetes mellitus patient.

PCT publication WO 03/082898 discloses C-terminal truncated fragments and N-terminal modified analogues of GIP, as well as various GIP analogues with a reduced peptide bond or alterations of the amino acids close to the DPPIV-specific cleavage site. This application further discloses analogues with different linkers between potential receptor binding sites of GIP. The compounds of this application are alleged to be useful in treating GIP-receptor mediated conditions, such as non-insulin dependent diabetes mellitus and obesity.

There exists a need for improved analogues of GIP, which are stable in formulation and have long plasma half-life in vivo resulting from decreased susceptibility to proteolysis and decreased clearance while maintaining binding affinity to a GIP receptor to elicit respective agonistic or antagonistic effects. Moreover, among other therapeutic effects of the compounds of the present invention as illustrated herein, tighter control of plasma glucose levels may prevent long-term diabetic complications, thereby providing an improved quality of life for patients.

SUMMARY OF THE INVENTION

In one aspect, the invention relates to peptide variants of GIP of the following formula (I):

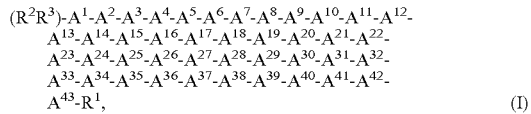

(I)

wherein:
A$^1$ is Cpa, His, 4Hppa, 2-Pal, 3-Pal, 4-Pal, (X$^4$, X$^5$, X$^6$, X$^7$, X$^8$)Phe, Taz, 3Thi, 7HO-Tic, Tyr(Ac), Tyr(Me), β-Tyr, 3Br-Tyr, 3,5Br-Tyr, 3Cl-Tyr, 2F-Tyr, 3F-Tyr, hTyr, 3I-Tyr, 3,5I-Tyr, αMe-Tyr, 2,6Me-Tyr, 3MeO-Tyr, 3NH$_2$-Tyr, 3NO$_2$-Tyr, 3OH-Tyr, or 3(HO—CH$_2$)Tyr;

A$^2$ is Ala, Abu, D-Abu, Acc, Aib, β-Ala, D-Ala, Gaba, Gly, Ser, D-Ser, Thr, D-Thr, Val, or D-Val;

A$^3$ is Glu, Aib, Asp, N-Me-Asp, Dhp, Dmt, N-Me-Glu, 3Hyp, 4Hyp, 4Ktp, Pro, hPro, Thz, or Tic;

A$^4$ is Gly, Acc, Aib, or β-Ala;

A$^5$ is Thr, Acc, Aib, or Ser;

A$^6$ is Phe, Acc, Aib, Aic, Cha, 1Nal, 2Nal, 2-Pal, 3-Pal, 4-Pal, (X$^4$, X$^5$, X$^6$, X$^7$, X$^8$)Phe, or Trp;

A$^7$ is Ile, Abu, Acc, Aib, Ala, Cha, Leu, Nle, Phe, Tle, or Val;

A$^8$ is Ser, Aib, or Thr;

A$^9$ is Asp, Aib, or Glu;

A$^{10}$ is Tyr, Acc, Cha, 1Nal, 2Nal, 2-Pal, 3-Pal, 4-Pal, Phe, or (X$^4$, X$^5$, X$^6$, X$^7$, X$^8$)Phe;

A$^{11}$ is Ser, Acc, Aib, Nle, or Thr;

A$^{12}$ is Ile, Abu, Acc, Aib, Ala, Cha, Leu, Nle, Phe, Tle, or Val;

A$^{13}$ is Ala, Acc, Aib, β-Ala, D-Ala, Gly, or Ser;

A$^{14}$ is Met, Abu, Acc, Aib, Ala, Cha, Ile, Leu, Nle, Phe, Tle, or Val;

A$^{15}$ is Asp, Aib, or Glu;

A$^{16}$ is Lys, Amp, Apc, Arg, hArg, Orn, HN—CH((CH$_2$)$_n$—N(R$^4$R$^8$))—C(O), Cys(succinimide-N-allyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$NH—C(O)—(CH$_2$)$_t$—CH$_3$), hCys(succinimide-N—(CH$_2$)$_s$—NH—C(O)—(CH$_2$)$_t$—CH$_3$), or Pen(succinimide-N—(CH$_2$)$_s$—NH—C(O)—(CH$_2$)$_t$—CH$_3$);

A$^{17}$ is Ile, Abu, Acc, Aib, Ala, Cha, Leu, Nle, Phe, Tle, or Val;

A$^{18}$ is His, Amp, Arg, 2-Pal, 3-Pal, 4-Pal, Phe, or Tyr;

A$^{19}$ is Gln, Aib, or Asn;

A$^{20}$ is Gln, Aib, or Asn;

A$^{21}$ is Asp, Aib, or Glu;

A$^{22}$ is Phe, Acc, Aib, Aic, Cha, 1Nal, 2Nal, 2-Pal, 3-Pal, 4-Pal, (X$^4$, X$^5$, X$^6$, X$^7$, X$^8$)Phe, or Trp;

A$^{23}$ is Val, Abu, Acc, Aib, Ala, Cha, Ile, Leu, Nle, or Tle;

A$^{24}$ is Asn, Aib, or Gln;

A$^{25}$ is Trp, Acc, Aib, 1Nal, 2Nal, 2-Pal, 3-Pal, 4-Pal, Phe, or (X$^4$, X$^5$, X$^6$, X$^7$, X$^8$)Phe;

A$^{26}$ is Leu, Acc, Aib, Cha, Ile, Nle, Phe, (X$^4$, X$^5$, X$^6$, X$^7$, X$^8$)Phe, or Tle;

A$^{27}$ is Leu, Acc, Aib, Cha, Ile, Nle, Phe, (X$^4$, X$^5$, X$^6$, X$^7$, X$^8$)Phe, or Tle;

A$^{28}$ is Ala, Acc, or Aib;

A$^{29}$ is Gln, Aib, Asn, or deleted;

A$^{30}$ is Lys, Amp, Apc, Arg, hArg, Orn, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_x$—NH—C(O)—(CH$_2$)$_t$—CH$_3$), hCys(succinimide-N—(CH$_2$)$_5$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{31}$ is Gly, Aib, Acc, β-Ala, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$NH—C(O)—(CH$_2$)$_t$—CH$_3$), hCys(succinimide-N—(CH$_2$), —NH—C(O)—(CH$_2$)$_t$—CH$_3$), Pen(succinimide-N—(CH$_2$), —NH—C(O)—(CH$_2$)$_t$—CH$_3$), or deleted;

A$^{32}$ is Lys, Amp, Apc, Arg, hArg, Orn, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_y$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{33}$ is Lys, Amp, Apc, Arg, hArg, Orn, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{34}$ is Asn, Aib, Gln, Ser, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$), —NH—C(O)—(CH$_2$)$_t$—CH$_3$), or deleted;

A$^{35}$ is Asp, Aib, Glu, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_s$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{36}$ is Trp, Acc, Aib, 1Nal, 2Nal, 2-Pal, 3-Pal, 4-Pal, Phe, (X$^4$, X$^5$, X$^6$, X$^7$, X$^8$)Phe, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$), —NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{37}$ is Lys, Amp, Apc, Arg, hArg, Orn, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{38}$ is His, Amp, 2-Pal, 3-Pal, 4-Pal, Phe, Tyr, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{39}$ is Asn, Aib, Gln, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{40}$ is Ile, Acc, Aib, Ser, Thr, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{41}$ is Thr, Acc, Aib, Asn, Gln, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$), —NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{42}$ is Gln, Acc, Aib, Asn, HN—CH((CH$_2$)$_n$—(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_n$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{43}$ is Acc, Ado, Aib, Ala, Asn, Asp, His, Gln, Phe, Thr, Trp, Orn(N—C(O)—(CH$_2$)$_{10}$—CH$_3$), HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_n$—NH—C(O)—(CH$_2$)$_t$—CH$_3$), or deleted;

R$^1$ is OH, NH$_2$, (C$_1$-C$_{30}$)alkoxy, or NH—X$^2$—CH$_2$—Z$^0$, wherein X$^2$ is a (C$_0$-C$_{30}$) hydrocarbon moiety and Z$^0$ is H, OH, CO$_2$H, or CONH$_2$;

each of R$^2$, R$^3$, R$^4$ and R$^5$ is independently selected from the group consisting of H, (C$_1$-C$_{30}$)alkyl, (C$_1$-C$_{30}$)heteroalkyl, (C$_1$-C$_{30}$)acyl, (C$_2$-C$_{30}$)alkenyl, (C$_2$-C$_{30}$)alkynyl, aryl(C$_1$-C$_{30}$)allyl, aryl(C$_1$-C$_{30}$)acyl, substituted (C$_1$-C$_{30}$)allyl, substituted (C$_1$-C$_{30}$)heteroalkyl, substituted (C$_1$-C$_{30}$)acyl, substituted (C$_2$-C$_{30}$)alkenyl, substituted (C$_2$-C$_{30}$)alkynyl, substituted aryl(C$_1$-C$_{30}$)allyl, and substituted aryl(C$_1$-C$_{30}$)acyl; provided that when R$^2$ is (C$_1$-C$_{30}$)acyl, aryl(C$_1$-C$_{30}$)acyl, substituted (C$_1$-C$_{30}$)acyl, or substituted aryl(C$_1$-C$_{30}$)acyl, then R$^3$ is H, (C$_1$-C$_{30}$)alkyl, (C$_1$-C$_{30}$)heteroalkyl, (C$_2$-C$_{30}$)alkenyl, (C$_2$-C$_{30}$)alkynyl, aryl(C$_1$-C$_{30}$)alkyl, substituted (C$_1$-C$_{30}$)alkyl, substituted (C$_1$-C$_{30}$)heteroalkyl, substituted (C$_2$-C$_{30}$)alkenyl, substituted (C$_2$-C$_{30}$)alkynyl, or substituted aryl(C$_1$-C$_{30}$)allyl; further provided that when R$^4$ is (C$_1$-C$_{30}$)acyl, aryl(C$_1$-C$_{30}$)acyl, substituted (C$_1$-C$_{30}$)acyl, or substituted aryl(C$_1$-C$_{30}$)acyl, then R$^5$ is H, (C$_1$-C$_{30}$)alkyl, (C$_1$-C$_{30}$)heteroalkyl, (C$_2$-C$_{30}$)alkenyl, (C$_2$-C$_{30}$)alkynyl, aryl(C$_1$-C$_{30}$)allyl, substituted (C$_1$-C$_{30}$)allyl, substituted (C$_1$-C$_{30}$)heteroalkyl, substituted (C$_2$-C$_{30}$)alkenyl, substituted (C$_2$-C$_{30}$)alkynyl, or substituted aryl(C$_1$-C$_{30}$)allyl;

n is, independently for each occurrence, an integer from 1 to 5 inclusive;

s, t, x and y each is, independently for each occurrence, an integer from 1 to 30 inclusive;

X$^4$, X$^5$, X$^6$, X$^7$ and X$^8$ each is, independently for each occurrence, H, F, CF$_3$, Cl, Br, I, (C$_{1-10}$)allyl, substituted (C$_{1-10}$)allyl, aryl, substituted aryl, OH, NH$_2$, —CH$_2$NH$_2$, NO$_2$, or CN;

provided that when A$^1$ is 4Hppa, then R$^2$ and R$^3$ are deleted;

further provided that more than one amino acid at positions 1, 2 and 3 of the compound are substituted or modified; and further provided that if the amino acid at position 1 is modified, it is not modified by:
(a) N-terminal alkylation;
(b) N-terminal acetylation;
(c) N-terminal acylation;
(d) the addition of an N-terminal isopropyl group; or
(e) the addition of an N-terminal pyroglutamic acid.

A subset (A) of the compounds covered by the above formula (I) are those in which:

A$^1$ is Cpa, His, 4Hppa, 2Pal, 3Pal, 4Pal, 3Br-Phe, 4CF$_3$-Phe, 3Cl-Phe, 4CN-Phe, 3F-Phe, 4F-Phe, 3,4F-Phe, 3,5F-Phe, 3,4,5F-Phe, 4Me-Phe, 4NH$_2$-Phe, 4NH$_2$CH$_2$-Phe, 3OH-Phe, Taz, 3Thi, 7HO-Tic, Tyr(Ac), Tyr(Me), β-Tyr, 3Br-Tyr, 3,5Br-Tyr, 3Cl-Tyr, 2F-Tyr, 3I-Tyr, hTyr, 3I-Tyr, 3,5I-Tyr, αMe-Tyr, 2,6Me-Tyr, 3MeO-Tyr, 3NH$_2$-Tyr, 3NO$_2$-Tyr, 3OH-Tyr, or 3(HO—CH$_2$)Tyr;

A$^2$ is Ala, Aib, Gly;
A$^3$ is Glu, 4Hyp, or hPro;
A$^4$ is Gly;
A$^5$ is Thr;
A$^6$ is Phe;
A$^2$ is Ile, A5c, or A6c;
A$^8$ is Ser;
A$^9$ is Asp;
A$^{10}$ is Tyr;

$A^{11}$ is Ser, A5c, or Aib;
$A^{12}$ is Ile;
$A^{13}$ is Ala or Aib;
$A^{14}$ is Met, A5c, or Nle;
$A^{15}$ is Asp;
$A^{16}$ is Lys;
$A^{17}$ is Ile;
$A^{18}$ is His;
$A^{19}$ is Gln;
$A^{20}$ is Gln;
$A^{21}$ is Asp;
$A^{22}$ is Phe;
$A^{23}$ is Val;
$A^{24}$ is Asn;
$A^{25}$ is Trp;
$A^{26}$ is Leu;
$A^{27}$ is Leu;
$A^{28}$ is Ala;
$A^{29}$ is Gln;
$A^{30}$ is Lys;
$A^{31}$ is Gly or deleted;
$A^{32}$ is Lys or deleted;
$A^{33}$ is Lys or deleted;
$A^{34}$ is Asn or deleted;
$A^{35}$ is Asp or deleted;
$A^{36}$ is Trp or deleted;
$A^{37}$ is Lys or deleted;
$A^{38}$ is His or deleted;
$A^{39}$ is Asn or deleted;
$A^{40}$ is Ile, A5c, or deleted;
$A^{41}$ is Thr, A5c, or deleted;
$A^{42}$ is Gln or deleted;
$A^{43}$ is His, Cys(succinimide-N—$(CH_2)_{11}$—$CH_3$), Orn (N—C(O)—$(CH_2)_{10}$—$CH_3$), or deleted; and
provided that the compound contains at least one amino acid substitution or modification at positions 4 to 43.

A subset of the compounds of the preceding subset (A) are those in which $A^1$ is 4Hppa; $A^{43}$ is deleted; and at least one of $A^2$, $A^3$, $A^7$, $A^{11}$ and $A^{14}$ is not the amino acid residue of the corresponding position in the native GIP.

Another subset (B) of the compounds of the preceding subset (A) are those in which $A^1$ is Tyr(Ac), Tyr(Me), β-Tyr, 3Br-Tyr, 3,5Br-Tyr, 3Cl-Tyr, 2F-Tyr, 3F-Tyr, hTyr, 3I-Tyr, 3,5I-Tyr, αMe-Tyr, 2,6Me-Tyr, 3MeO-Tyr, 3NH$_2$-Tyr, 3NO$_2$-Tyr, 3OH-Tyr, or 3(HO—CH$_2$)Tyr; $A^2$ is A5c, A6c, Aib, D-Ala, Gly, or Ser; and at least one of $A^3$, $A^{11}$, $A^{13}$, $A^{14}$, $A^{40}$, $A^{41}$ and $A^{43}$ is not the amino acid residue of the corresponding position in the native GIP.

A subset of the compounds of the preceding subset (B) are those in which $A^2$ is Aib, D-Ala, or Gly; and at least two of $A^3$, $A^{11}$, $A^{13}$, $A^{14}$, $A^{40}$, $A^{41}$ and $A^{43}$ are not the amino acid residues of the corresponding positions in the native GIP.

Another subset (C) of the compounds of the preceding subset (A) are those in which $A^1$ is 3Br-Phe, 3Cl-Phe, 4CN-Phe, 3F-Phe, 4F-Phe, 3,4F-Phe, 3,4,5F-Phe, 3,5F-Phe, 4NH$_2$-Phe, 4NH$_2$CH$_2$-Phe, or 3OH-Phe; $A^2$ is A5c, A6c, Aib, D-Ala, Gly, or Ser; $A^{11}$ is A5c; and at least one of $A^{14}$ and $A^{41}$ is not the amino acid residue of the corresponding position in the native GIP.

A subset of the compounds of the preceding subset (C) is that in which $A^2$ is Aib.

Another aspect of the present invention relates to peptide variants of GIP covered by the above formula (I), wherein the peptide bond between $A^1$ and $A^2$ is replaced by a pseudopeptide bond, wherein $A^1$-$A^2$ is $A^1$-Ψ-(CH$_2$—NH)$A^2$.

Preferred compounds of the present invention are:
Example 1: (4Hppa$^1$, Aib$^2$, A5c$^7$, Nle$^{14}$)hGIP(1-30)-NH$_2$ (SEQ ID NO:4);
Example 2: (4Hppa$^1$, Aib$^{2,11}$, Nle$^{14}$)hGIP(1-30)-NH$_2$ (SEQ ID NO:5);
Example 3: (4Hppa$^1$, Aib$^2$, A5c$^7$)hGIP(1-30)-NH$_2$ (SEQ ID NO:6);
Example 4: (4Hppa$^1$, Aib$^{2,11}$)hGIP(1-30)-NH$_2$ (SEQ ID NO:7);
Example 5: (4Hppa$^1$, Aib$^2$, Nle$^{14}$)hGIP(1-30)-NH$_2$ (SEQ ID NO:8);
Example 6: (4Hppa$^1$, Aib$^2$)hGIP(1-30)-NH$_2$(SEQ ID NO:9);
Example 7: (4Hppa$^1$, 4Hyp$^3$, A6c$^7$)hGIP(1-42)-OH (SEQ ID NO:10);
Example 8: (4Hppa$^1$, hPro$^3$, A6c$^7$)hGIP(1-42)-OH (SEQ ID NO:11);
Example 9: (4Hppa$^1$, Aib$^2$, hPro$^3$, Nle$^{14}$)hGIP(1-30)-NH$_2$ (SEQ ID NO:12);
Example 10: (His$^1$, Aib$^{2, 13}$, Nle$^{14}$)hGIP(1-42)-OH (SEQ ID NO:13);
Example 11: (3,5Br-Tyr$^1$, Aib$^{2, 13}$, Nle$^{14}$)hGIP(1-42)-OH (SEQ ID NO:14);
Example 12: (His$^1$, Aib$^2$, A5c$^{11}$, Nle$^{14}$)hGIP(1-42)-OH (SEQ ID NO:15);
Example 13: (3,5Br-Tyr$^1$, Aib$^2$, A5c$^{11}$, Nle$^{14}$)hGIP(1-42)-OH (SEQ ID NO:16);
Example 14: (3Cl-Tyr$^1$, Aib$^2$, A5c$^{11}$, Nle$^{14}$)hGIP(1-42)-OH (SEQ ID NO:17);
Example 15: (3Br-Tyr$^1$, Aib$^2$, A5c$^{11}$, Nle$^{14}$)hGIP(1-42)-OH (SEQ ID NO:18);
Example 16: (3I-Tyr$^1$, Aib$^2$, A5c$^{11}$, Nle$^{14}$)hGIP(1-42)-OH (SEQ ID NO:19);
Example 17: (3,5I-Tyr$^1$, Aib$^2$, A5c$^{11}$, Nle$^{14}$)hGIP(1-42)-OH (SEQ ID NO:20);
Example 18: (4NH$_2$-Phe$^1$, Aib$^2$, A5c$^{11}$, Nle$^{14}$)hGIP(1-42)-OH (SEQ ID NO:21);
Example 19: (hTyr$^1$, Aib$^2$, A5c$^{11}$, Nle$^{14}$)hGIP(1-42)-OH (SEQ ID NO:22);
Example 20: (Cpa$^1$, Aib$^2$, A5c$^{11}$, Nle$^{14}$)hGIP(1-42)-OH (SEQ ID NO:23);
Example 21: (4NH$_2$CH$_2$-Phe$^1$, Aib$^2$, A5c$^{11}$, Nle$^{14}$)hGIP(1-42)-OH (SEQ ID NO:24);
Example 22: (3,4,5F-Phe$^1$, Aib$^2$, A5c$^{11}$, Nle$^{14}$)hGIP(1-42)-OH (SEQ ID NO:25);
Example 23: (3F-Phe$^1$, Aib$^2$, A5c$^{11}$, Nle$^{14}$)hGIP(1-42)-OH (SEQ ID NO:26);
Example 24: (3,4F-Phe$^1$, Aib$^2$, A5c$^{11}$, Nle$^{14}$)hGIP(1-42)-OH (SEQ ID NO:27);
Example 25: (3,5F-Phe$^1$, Aib$^2$, A5c$^{11}$, Nle$^{14}$)hGIP(1-42)-OH (SEQ ID NO:28);
Example 26: (3OH-Phe$^1$, Aib$^2$, A5c$^{11, 41}$)hGIP(1-42)-OH (SEQ ID NO:29);
Example 27: (3OH-Tyr$^1$, Aib$^2$, A5c$^{11, 41}$)hGIP(1-42)-OH (SEQ ID NO:30);
Example 28: (3MeO-Tyr$^1$, Aib$^2$, A5c$^{11, 41}$)hGIP(1-42)-OH (SEQ ID NO:31);
Example 29: [Tyr(Ac)$^1$, Aib$^2$, A5c$^{11, 41}$]hGIP(1-42)-OH (SEQ ID NO:32);
Example 30: (2,6Me-Tyr$^1$, Aib$^2$, A5c$^{11, 41}$)hGIP(1-42)-OH (SEQ ID NO:33);
Example 31: [Tyr(Me)$^1$, Aib$^2$, A5c$^{11, 41}$]hGIP(1-42)-OH (SEQ ID NO:34);
Example 32: (4F-Phe$^1$, Aib$^2$, A5c$^{11, 41}$)hGIP(1-42)-OH (SEQ ID NO:35);
Example 33: (4-Pal$^1$, Aib$^2$, A5c$^{11, 41}$)hGIP(1-42)-OH (SEQ ID NO:36);

Example 34: (3-Pal$^1$, Aib$^2$, A5c$^{11, 41}$)hGIP(1-42)-OH (SEQ ID NO:37);
Example 35: (Taz$^1$, Aib$^2$, A5c$^{11, 41}$)hGIP(1-42)-OH (SEQ ID NO:38);
Example 36: (3NO$_2$-Tyr$^1$, Aib$^2$, A5c$^{11, 41}$)hGIP(1-42)-OH (SEQ ID NO:39);
Example 37: (3Thi$^1$, Aib$^2$, A5c$^{11, 41}$)hGIP(1-42)-OH (SEQ ID NO:40);
Example 38: (4CN-Phe$^1$, Aib$^2$, A5c$^{11, 41}$)hGIP(1-42)-OH (SEQ ID NO:41);
Example 39: (3F-Tyr$^1$, Gly$^2$, A5c$^{11, 41}$)hGIP(1-42)-OH (SEQ ID NO:42);
Example 40: [Tyr$^1$-Ψ-(CH$_2$—NH)Gly$^2$, A5c$^{11, 41}$]hGIP(1-42)-OH (SEQ ID NO:43);
Example 41: (3F-Phe$^1$, Aib$^2$, A5c$^{11, 41}$)hGIP(1-42)-OH (SEQ ID NO:44);
Example 42: (3Cl-Phe$^1$, Aib$^2$, A5c$^{11, 41}$)hGIP(1-42)-OH (SEQ ID NO:45);
Example 43: (3Br-Phe$^1$, Aib$^2$, A5c$^{11, 41}$)hGIP(1-42)-OH (SEQ ID NO:46);
Example 44: (3Cl-Tyr$^1$, Aib$^2$, A5c$^{11, 41}$)hGIP(1-42)-OH (SEQ ID NO:47);
Example 45: (3Br-Tyr$^1$, Aib$^2$, A5c$^{11, 41}$)hGIP(1-42)-OH (SEQ ID NO:48);
Example 46: (β-Tyr$^1$, Aib$^2$, A5c$^{11, 41}$)haP(1-42)-OH (SEQ ID NO:49);
Example 47: (3F-Tyr$^1$, Aib$^2$, A5c$^{11, 41}$)hGIP(1-42)-OH (SEQ ID NO:50);
Example 48: (2F-Tyr$^1$, Aib$^2$, A5c$^{11, 41}$)hGIP(1-42)-OH (SEQ ID NO:51);
Example 49: (αMe-Tyr$^1$, Aib$^2$, A5c$^{11, 41}$)hGIP(1-42)-OH (SEQ ID NO:52);
Example 50: (3NH$_2$-Tyr$^1$, Aib$^2$, A5c$^{11, 41}$)hGIP(1-42)-OH (SEQ ID NO:53);
Example 51: (2-Pal$^1$, Aib$^2$, A5c$^{11, 41}$)hGIP(1-42)-OH (SEQ ID NO:54);
Example 52: [3(HO—CH$_2$)Tyr$^1$, Aib$^2$, A5c$^{11, 41}$]hGIP(1-42)-OH (SEQ ID NO:55);
Example 53: (2,6Me-Tyr$^1$, Aib$^2$, A5c$^{11}$, His$^{43}$)hGIP(1-43)-OH (SEQ ID NO:56);
Example 54: (2,6Me-Tyr$^1$, Aib$^2$, A5c$^{11, 14}$, His$^{43}$)hGIP(1-43)-OH (SEQ ID NO:57);
Example 55: (2,6Me-Tyr$^1$, Aib$^2$, A5c$^{11}$, Nle$^{14}$, His$^{43}$)hGIP(1-43)-OH (SEQ ID NO:58);
Example 56: (3F-Phe$^1$, Aib$^2$, A5c$^{11, 14, 41}$)hGIP(1-42)-OH (SEQ ID NO:59);
Example 57: (3F-Phe$^1$, Aib$^2$, A5c$^{11, 41}$, Nle$^{14}$, His$^{43}$)hGIP(1-43)-OH (SEQ ID NO:60);
Example 58: (3F-Phe$^1$, Aib$^2$, A5c$^{11, 41}$, His$^{43}$)hGIP(1-43)-OH (SEQ ID NO:61);
Example 59: (3F-Phe$^1$, Aib$^2$, A5c$^{11, 14, 41}$, His$^{43}$)hGIP(1-43)-OH (SEQ ID NO:62);
Example 60: deleted
Example 61: (3Cl-Tyr$^1$, D-Ala$^2$, A5c$^{11}$, Nle$^{14}$, His$^{43}$)hGIP(1-43)-OH;
Example 62: (3Cl-Tyr$^1$, D-Ala$^2$, A5c$^{11, 14}$, His$^{43}$)hGIP(1-43)-OH;
Example 63: (3Cl-Tyr$^1$, Aib$^2$, A5c$^{11, 14}$, His$^{43}$)hGIP(1-43)-OH (SEQ ID NO:63);
Example 64: (3Cl-Tyr$^1$, Aib$^2$, A5c$^{11}$, Nle$^{14}$, His$^{43}$)hGIP(1-43)-OH (SEQ ID NO:64);
Example 65: [3Cl-Tyr$^1$, Aib$^2$, A5c$^{11}$, Nle$^{14}$, Orn$^{43}$(N—C(O)—(CH$_2$)$_{10}$—CH$_3$)]hGIP(1-43)-OH (SEQ ID NO:65);
Example 66: [3Cl-Tyr$^1$, Aib$^2$, A5c$^{11}$, Nle$^{14}$, Cys$^{43}$(succinimide-N—(CH$_2$)$_{11}$—CH$_3$)]hGIP(1-43)-OH (SEQ ID NO:66);
Example 67: [3Cl-Tyr$^1$, D-Ala$^2$, A5c$^{11}$, Nle$^{14}$, Orn$^{43}$(N—C(O)—(CH$_2$)$_{10}$—CH$_3$)]hGIP(1-43)-OH;
Example 68: [3Cl-Tyr$^1$, D-Ala$^2$, A5c$^{11}$, Nle$^{14}$, Cys$^{43}$(succinimide-N—(CH$_2$)$_{11}$—CH$_3$)]hGIP(1-43)-OH;
Example 69: [3Cl-Tyr$^1$, D-Ala$^2$, A5c$^{11, 14}$, Orn$^{43}$(N—C(O)—(CH$_2$)$_{10}$—CH$_3$)]hGIP(1-43)-OH;
Example 70: [3Cl-Tyr$^1$, D-Ala$^2$, A5c$^{11, 14}$, Cys$^{43}$(succinimide-N—(CH$_2$)$_{11}$—CH$_3$)]hGIP(1-43)-OH;
Example 71: (3Br-Tyr$^1$, Aib$^2$, A5c$^{11}$, Nle$^{14}$, His$^{43}$)hGIP(1-43)-OH (SEQ ID NO:67);
Example 72: (3Br-Tyr$^1$, Aib$^2$, A5c$^{11, 14}$, His$^{43}$)hGIP(1-43)-OH (SEQ ID NO:68);
Example 73: (3MeO-Tyr$^1$, Aib$^2$, A5c$^{11}$, His$^{43}$)hGIP(1-43)-OH (SEQ ID NO:69);
Example 74: (3MeO-Tyr$^1$, Aib$^2$, A5c$^{11, 14}$, His$^{43}$)hGIP(1-43)-OH (SEQ ID NO:70);
Example 75: (3MeO-Tyr$^1$, Aib$^2$, A5c$^{11, 14}$, His$^{43}$)hGIP(1-43)-OH (SEQ ED NO:71);
Example 76: (4CF$_3$-Phe$^1$, Aib$^2$, A5c$^{11}$, His$^{43}$)hGIP(1-43)-OH (SEQ ID NO:72);
Example 77: (7HO-Tic$^1$, Aib$^2$, A5c$^{11}$, His$^{43}$)hGIP(1-43)-OH (SEQ ID NO:73);
Example 78: (4Me-Phe$^1$, Aib$^2$, A5c$^{11}$, His$^{43}$)hGIP(1-43)-OH (SEQ ID NO:74);
Example 79: (4CN-Phe$^1$, Aib$^2$, A5c$^{11}$, His$^{43}$)hGIP(1-43)-OH (SEQ ID NO:75);
Example 80: (hTyr$^1$, Aib$^2$, A5c$^{11}$, His$^{43}$)hGIP(1-43)-OH (SEQ ID NO:76);
Example 81: [3Cl-Tyr$^1$, D-Ala$^2$, A5c$^{11}$, Nle$^{14}$, Lys$^{43}$(N—C(O)—(CH$_2$)$_{10}$—CH$_3$)]hGIP(1-43)-OH;
Example 82: [3Cl-Tyr$^1$, D-Ala$^2$, A5c$^{11, 14}$, Lys$^{43}$(N—C(O)—(CH$_2$)$_{10}$—CH$_3$)]hGIP(1-43)-OH;
Example 83: [3Cl-Tyr$^1$, Aib$^2$, A5c$^{11}$, Nle$^{14}$, Lys$^{43}$(N—C(O)—(CH$_2$)$_{10}$—CH$_3$)]hGIP(1-43)-OH (SEQ ID NO:77);
Example 84: [3Cl-Tyr$^1$, Aib$^2$, A5c$^{11, 14}$, Lys$^{43}$(N—C(O)—(CH$_2$)$_{10}$—CH$_3$)]hGIP(1-43)-OH (SEQ ID NO:78);
Example 85: (3Cl-Tyr$^1$, Aib$^2$, A5c$^{11}$, Nle$^{14}$, Cys$^{43}$)hGIP(1-43)-OH (SEQ ID NO:79);
Example 86: [3Cl-Tyr$^1$, D-Ala$^2$, A5c$^{11}$, Nle$^{14}$, Cys$^{43}$(succinimide)]hGIP(1-43)-OH; and
Example 87: [3Cl-Tyr$^1$, D-Ala$^2$, A5c$^{11, 14}$, Cys$^{43}$(succinimide)]hGIP(1-43)-OH.

According to another aspect of the present invention, a compound according to the present invention as summarized hereinabove and claimed in the appended claims may further comprise a covalently linked PEG moiety, in which said PEG moiety is covalently linked to the compound via a Cys(maleimide), hCys(maleimide), or Pen(maleimide) linker, to form Cys(succinimide-N-PEG), hCys(succinimide-N-PEG), or Pen(succinimide-N-PEG), wherein "succinimide-N-PEG" is either linear or branched as defined hereinbelow. Such PEG moiety has average molecular weight of from about 2,000 to about 80,000, and preferably such PEG moiety is selected from the group consisting of 5K PEG, 10K PEG, 20K PEG, 30K PEG, 40K PEG, 50K PEG, and 60K PEG, to form Cys(succinimide-N-5K PEG), Cys(succinimide-N-10K PEG), Cys(succinimide-N-20K PEG), Cys(succinimide-N-30K PEG), Cys(succinimide-N-40K PEG), Cys(succinimide-N-50K PEG), Cys(succinimide-N-60K PEG), hCys(succinimide-N-5K PEG), hCys(succinimide-N-10K PEG), hCys(succinimide-N-20K PEG), hCys(succinimide-N-30K PEG), hCys(succinimide-N-40K PEG), hCys(succinimide-N-50K PEG), hCys(succinimide-N-60K PEG), Pen(succinimide-N-5K PEG), Pen(succinimide-N-10K PEG), Pen(succinimide-N-20K PEG), Pen(succinimide-N-30K PEG), Pen(succinimide-N-40K PEG), Pen(succinimide-N-50K PEG), or Pen(succinimide-N-60K PEG).

PEGylation occurs at any one of amino acid residue positions 16, 30, and 31-43, and preferably at any one of amino acid residue positions 32, 33 and 43, whereby Cys(succinimide-N-PEG), hCys(succinimide-N-PEG), or Pen(succinimide-N-PEG) is placed in any one of such amino acid residue positions.

Further, the above formula (I) may be expanded to provide PEGylation sites at positions $A^{44}$-$A^{47}$. The C-terminus of such PEGylated compounds of the present invention may be amidated, e.g., (4Hppa$^1$, Aib$^2$, A5c$^7$, Nle$^{14}$)hGIP(1-30)-NH$_2$ (SEQ ID NO:4), or it may remain as free acid, e.g., (4Hppa$^1$, Aib$^2$, A5c$^7$, Nle$^{14}$)hGIP(1-30)-OH (SEQ ID NO:96).

Preferred compounds of such PEGylated compounds are:

Example 88: [3Cl-Tyr$^1$, Aib$^2$, A5c$^{11}$, Nle$^{14}$, Cys$^{43}$(succinimide-N-20K PEG)]hGIP(1-43)-NH$_2$ (SEQ ID NO:80);

Example 89: [3Cl-Tyr$^1$, Aib$^2$, A5c$^{11}$, Nle$^{14}$, Cys$^{43}$(succinimide-N-30K PEG)]hGIP(1-43)-NH$_2$ (SEQ ID NO:81);

Example 90: [3Cl-Tyr$^1$, D-Ala$^2$, A5c$^{11}$, Nle$^{14}$, Cys$^{43}$(succinimide-N-20K PEG)]hGIP(1-43)-NH$_2$;

Example 91: [3Cl-Tyr$^1$, D-Ala$^2$, A5c$^{11}$, Nle$^{14}$, Cys$^{43}$(succinimide-N-30K PEG)]hGIP(1-43)-NH$_2$;

Example 92: [3Cl-Tyr$^1$, Aib$^2$, A5c$^H$, Nle$^{14}$, Cys$^{43}$(succinimide-N-60K PEG)]hGIP(1-43)-NH$_2$ (SEQ ID NO:82);

Example 93: [3Cl-Tyr$^1$, Aib$^2$, A5c$^{11, 14}$, Cys$^{43}$(succinimide-N-60K PEG)]hGIP(1-43)-NH$_2$ (SEQ ID NO:83);

Example 94: [3Cl-Tyr$^1$, D-Ala$^2$, A5c$^{11}$, Nle$^{14}$, Cys$^{43}$(succinimide-N-60K PEG)]hGIP(1-43)-NH$_2$;

Example 95: [3Cl-Tyr$^1$, D-Ala$^2$, A5c$^{11, 14}$, Cys$^{43}$(succinimide-N-60K PEG)]hGIP(1-43)-NH$_2$;

Example 96: [3Cl-Tyr$^1$, Aib$^2$, A5c$^{11}$, Nle$^{14}$, Cys$^{43}$(succinimide-N—(CH$_2$)$_2$—C(O)NH—(CH$_2$)$_3$-20K PEG)]hGIP(1-43)-NH$_2$ (SEQ ID NO:84);

Example 97: [3Cl-Tyr$^1$, Aib$^2$, A5c$^{11}$, Nle$^{14}$, Cys$^{32}$(succinimide-N—(CH$_2$)$_2$—C(O)NH—(CH$_2$)$_3$-20K PEG)]hGIP(1-42)-NH$_2$ (SEQ ID NO:85);

Example 98: [3Cl-Tyr$^1$, Aib$^2$, A5c$^{11}$, Nle$^{14}$, Cys$^{33}$(succinimide-N—(CH$_2$)$_2$—C(O)NH—(CH$_2$)$_3$-20K PEG)]hGIP(1-42)-NH$_2$ (SEQ ID NO:86);

Example 99: [3Cl-Tyr$^1$, D-Ala$^2$, A5c$^{11}$, Nle$^{14}$, Cys$^{43}$(succinimide-N—(CH$_2$)$_2$—C(O)NH—(CH$_2$)$_3$-20K PEG)]hGIP(1-43)-NH$_2$;

Example 100: [3Cl-Tyr$^1$, D-Ala$^2$, A5c$^{11}$, Nle$^{14}$, Cys$^{32}$(succinimide-N—(CH$_2$)$_2$—C(O)NH—(CH$_2$)$_3$-20K PEG)]hGIP(1-42)-NH$_2$;

Example 101: [3Cl-Tyr$^1$, D-Ala$^2$, A5c$^{11}$, Nle$^{14}$, Cys$^{33}$(succinimide-N—(CH$_2$)$_2$—C(O)NH—(CH$_2$)$_3$-20K PEG)]hGIP(1-42)-NH$_2$;

Example 102: [3Cl-Tyr$^1$, Aib$^2$, A5c$^{11}$, Cys$^{43}$(succinimide-N—(CH$_2$)$_2$—C(O)NH—(CH$_2$)$_3$—O—CH$_2$—CH(20K PEG)-CH$_2$-20K PEG)]hGIP(1-43)-NH$_2$ (SEQ ID NO:87);

Example 103: [3C$_1$-Tyr$^1$, Aib$^2$, A5c$^{11}$, Nle$^{14}$, Cys$^{32}$(succinimide-N—(CH$_2$)$_2$—C(O)NH—(CH$_2$)$_3$—O—CH$_2$—CH(20K PEG)-CH$_2$-20K PEG)]hGIP(1-42)-NH$_2$ (SEQ ID NO:88);

Example 104: [3Cl-Tyr$^1$, Aib$^2$, Nle$^{14}$, Cys$^{33}$(succinimide-N—(CH$_2$)$_2$—C(O)NH—(CH$_2$)$_3$—O—CH$_2$—CH(20K PEG)-CH$_2$-20K PEG)]hGIP(1-42)-NH$_2$ (SEQ ID NO:89);

Example 105: [3Cl-Tyr$^1$, A5c$^{11}$, Nle$^{14}$, Cys$^{43}$(succinimide-N—(CH$_2$)$_2$—C(O)NH—(CH$_2$)$_3$—O—CH$_2$—CH(20K PEG)-CH$_2$-20K PEG)]hGIP(1-43)-NH$_2$;

Example 106: [3Cl-Tyr$^1$, D-Ala$^2$, A5c$^{11}$, Nle$^{14}$, Cys$^{32}$(succinimide-N—(CH$_2$)$_2$—C(O)NH—(CH$_2$)$_3$—O—CH$_2$—CH(20K PEG)-CH$_2$-20K PEG)]hGIP(1-42)-NH$_2$;

Example 107: [3Cl-Tyr$^1$, D-Ala$^2$, A5c$^{11}$, Nle$^{14}$, Cys$^{33}$(succinimide-N—(CH$_2$)$_2$—C(O)NH—(CH$_2$)$_3$—O—CH$_2$—CH(20K PEG)-CH$_2$-20K PEG)]hGIP(1-42)-NH$_2$;

Example 108: [3Cl-Tyr$^1$, Aib$^2$, A5c$^{11}$, Nle$^{14}$, Cys$^{43}$(succinimide-N—(CH$_2$)$_2$—C(O)NH—(CH$_2$)$_{3-20}$K PEG)]hGIP(1-43)-NH$_2$ (SEQ ID NO:90);

Example 109: [3Cl-Tyr$^1$, Aib$^2$, A5c$^{11, 14}$, Cys$^{32}$(succinimide-N—(CH$_2$)$_2$—C(O)NH—(CH$_2$)$_3$-20K PEG)]hGIP(1-42)-NH$_2$ (SEQ ID NO:91);

Example 110: [3Cl-Tyr$^1$, Aib$^2$, A5c$^{11, 14}$, Cys$^{33}$(succinimide-N—(CH$_2$)$_2$—C(O)NH—(CH$_2$)$_3$-20K PEG)]hGIP(1-42)-NH$_2$ (SEQ ID NO:92);

Example 111: [3Cl-Tyr$^1$, D-Ala$^2$, A5c$^{11, 14}$, Cys$^{43}$(succinimide-N—(CH$_2$)$_2$—C(O)NH—(CH$_2$)$_3$-20K PEG)]hGIP(1-43)-NH$_2$;

Example 112: [3Cl-Tyr$^1$, D-Ala$^2$, A5c$^{11, 14}$, Cys$^{32}$(succinimide-N—(CH$_2$)$_2$—C(O)NH—(CH$_2$)$_{3-20}$K PEG)]hGIP(1-42)-NH$_2$;

Example 113: [3Cl-Tyr$^1$, D-Ala$^2$, A5c$^{11, 14}$, Cys$^{33}$(succinimide-N—(CH$_2$)$_2$—C(O)NH—(CH$_2$)$_{3-20}$K PEG)]hGIP(1-42)-NH$_2$;

Example 114: [3Cl-Tyr$^1$, Aib$^2$, A5c$^{11, 14}$, Cys$^{43}$(succinimide-N—(CH$_2$)$_2$—C(O)NH—(CH$_2$)$_3$—O—CH$_2$—CH(20K PEG)-CH$_2$-20K PEG)]hGIP(1-43)-NH$_2$ (SEQ ID NO:93);

Example 115: [3Cl-Tyr$^1$, Aib$^2$, A5c$^{11, 14}$, Cys$^{32}$(succinimide-N—(CH$_2$)$_2$—C(O)NH—(CH$_2$)$_3$—O—CH$_2$—CH(20K PEG)-CH$_2$-20K PEG)]hGIP(1-42)-NH$_2$ (SEQ ID NO:94);

Example 116: [3Cl-Tyr$^1$, Aib$^2$, A5c$^{11, 14}$, Cys$^{33}$(succinimide-N—(CH$_2$)$_2$—C(O)NH—(CH$_2$)$_3$—O—CH$_2$—CH(20K PEG)-CH$_2$-20K PEG)]hGIP(1-42)-NH$_2$ (SEQ ID NO:95);

Example 117: [30-Tyr$^1$, D-Ala$^2$, A5c$^{11, 14}$, Cys$^{43}$(succinimide-N—(CH$_2$)$_2$—C(O)NH—(CH$_2$)$_3$—O—CH$_2$—CH(20K PEG)-CH$_2$-20K PEG)]hGIP(1-43)-NH$_2$;

Example 118: [3Cl-Tyr$^1$, D-Ala$^2$, A5c$^{11, 14}$, Cys$^{32}$(succinimide-N—(CH$_2$)$_2$—C(O)NH—(CH$_2$)$_3$—O—CH$_2$—CH(20K PEG)-CH$_2$-20K PEG)]hGIP(1-42)-NH$_2$; and Example 119: [3Cl-Tyr$^1$, D-Ala$^2$, A5c$^{11, 14}$, Cys$^{33}$(succinimide-N—(CH$_2$)$_2$—C(O)NH—(CH$_2$)$_3$—O—CH$_2$—CH(20K PEG)-CH$_2$-20K PEG)]hGIP(1-42)-NH$_2$.

DETAILED DESCRIPTION OF THE INVENTION

The application employs the following commonly understood abbreviations:

Abu: α-aminobutyric acid
Acc: 1-amino-1-cyclo($C_3$-$C_9$)alkyl carboxylic acid
   A3c: 1-amino-1-cyclopropanecarboxylic acid
   A4c: 1-amino-1-cyclobutanecarboxylic acid
   A5c: 1-amino-1-cyclopentanecarboxylic acid
   A6c: 1-amino-1-cyclohexanecarboxylic acid
Act: 4-amino-4-carboxytetrahydropyran
Ado: 12-aminododecanoic acid
Aib: α-aminoisobutyric acid
Aic: 2-aminoindan-2-carboxylic acid
Ala or A: alanine
β-Ala: beta-alanine
Amp: 4-amino-phenylalanine;
Apc: 4-amino-4-carboxypiperidine:
Arg or R: arginine
hArg: homoarginine
Asn or N: asparagine
Asp or D: aspartic acid
Aun: 11-aminoundecanoic acid
Ava: 5-aminovaleric acid
Cha: β-cyclohexylalanine
Cpa: 4-Cl-phenylalanine
Cys or C: cysteine
Dhp: 3,4-dehydroproline
Dmt: 5,5-dimethylthiazolidine-4-carboxylic acid
Gaba: γ-aminobutyric acid Gln or Q: glutamine
Glu or E: glutamic acid
Gly or G: glycine
His or H: histidine
4Hppa: 3-(4-hydroxyphenyl)propionic acid
3Hyp: 3-hydroxyproline
4Hyp: 4-hydroxyproline
Ile or I: isoleucine
4Ktp: 4-ketoproline
Leu or L: leucine
Lys or K: lysine
Met or M: methionine
Nle: norleucine
Nme-Tyr: N-methyl-tyrosine
1 Nal or 1-Nal: β-(1-naphthyl)alanine
2Nal or 2-Nal: β-(2-naphthyl)alanine
Nle: norleucine
Nva: norvaline
Orn: ornithine
2Pal or 2-Pal: β-(2-pyridinyl)alanine
3Pal or 3-Pal: β-(3-pyridinyl)alanine
4Pal or 4-Pal: β-(4-pyridinyl)alanine
Pen: penicillamine
Phe or F: phenylalanine
(3,4,5F)Phe: 3,4,5-trifluorophenylalanine
(2,3,4,5,6)Phe: 2,3,4,5,6-pentafluorophenylalanine
3,4,5F-Phe: 3,4,5-trifluoro-phenylalanine
3,4F-Phe: 3,4-difluoro-phenylalanine
3,5F-Phe: 3,5-difluoro-phenylalanine
3Br-Phe: 3-bromo-phenylalanine
3Cl-Phe: 3-chloro-phenylalanine
3F-Phe: 3-fluoro-phenylalanine
3OH-Phe: 3-hydroxy-phenylalanine
4CN-Phe: 4-cyano-phenylalanine
4F-Phe: 4-fluoro-phenylalanine
4NH$_2$CH$_2$-Phe: 4-aminomethyl-phenylalanine
4NH$_2$-Phe: 4-amino-phenylalanine
Pro or P: proline
hPro: homoproline
Psu: N-propylsuccinimide
Ser or S: serine
Taz: β-(4-thiazolyl)alanine
3Thi or 3-Thi: β-(3-thienyl)alanine
Thr or T: threonine
Thz: thioproline
Tic: tetrahydroisoquinoline-3-carboxylic acid
Tle: tert-leucine
Trp or W: tryptophan
Tyr or Y: tyrosine
Tyr(Ac): tyrosine(acetyl)
Tyr(Me): tyrosine(O-methyl)
β-Tyr: β-tyrosine
αMe-Tyr: α-methyl-tyrosine
2,6Me-Tyr: 2,6-dimethyl-tyrosine
2F-Tyr: 2-fluoro-tyrosine
3,5Br-Tyr: 3,5-dibromo-tyrosine
3,5I-Tyr: 3,5-diiodo-tyrosine
3Br-Tyr: 3-bromo-tyrosine
3Cl-Tyr: 3-chloro-tyrosine
3F-Tyr: 3-fluoro-tyrosine
3I-Tyr: 3-iodo-tyrosine
3MeO-Tyr: 3-O-methyl-tyrosine
3NH$_2$-Tyr: 3-amino-tyrosine
3NO$_2$-Tyr: 3-nitro-tyrosine
3 (OH—CH$_2$)Tyr: 3-methylhydroxy-tyrosine
3OH-Tyr: 3-hydroxy-tyrosine
Val or V: valine Certain other abbreviations used herein are defined as follows:
Boc: tert-butyloxycarbonyl
BSA: bovine serum albumin
DCM: dichloromethane
DIPEA: diisopropylethyl amine
DMF: dimethylformamide
ESI: electrospray ionization
Fmoc: 9-Fluorenylmethyloxycarbonyl
HBTU: 2-(1H-benzotriazole-1-yl)-1,1,3,3-tetramethyluroniumhexafluorophosphate
HOBT: 1-hydroxybenzotriazole
HPLC: high performance liquid chromatography
IBMX: isobutylmethylxanthine
LC-MS: liquid chromatography-mass spectrometry
NMP: N-methylpyrrolidone
5K PEG: polyethylene glycol, which may include other functional groups or moieties such as a linker, and which is either linear or branched as defined hereinbelow, with an average total molecular weight of about 5,000
10K PEG: polyethylene glycol, which may include other functional groups or moieties such as a linker, and which is either linear or branched as defined hereinbelow, with an average total molecular weight of about 10,000
20K PEG: polyethylene glycol, which may include other functional groups or moieties such as a linker, and which is either linear or branched as defined hereinbelow, with an average total molecular weight of about 20,000
30K PEG: polyethylene glycol, which may include other functional groups or moieties such as a linker, and which is either linear or branched as defined hereinbelow, with an average total molecular weight of about 30,000
40K PEG: polyethylene glycol, which may include other functional groups or moieties such as a linker, and which is either linear or branched as defined hereinbelow, with an average total molecular weight of about 40,000
50K PEG: polyethylene glycol, which may include other functional groups or moieties such as a linker, and which is either linear or branched as defined hereinbelow, with an average total molecular weight of about 50,000
60K PEG: polyethylene glycol, which may include other functional groups or moieties such as a linker, and which is either linear or branched as defined hereinbelow, with an average total molecular weight of about 60,000
tBu: tert-butyl
TIS: triisopropylsilane
Trt: trityl
TFA: trifluoro acetic acid
TFFH: tetramethylfluoroformamidinium hexafluorophosphate
Z: benzyloxycarbonyl
"4CF$_3$-Phe", i.e., 4-trifluoromethyl-phenylalanine, has the structure of:

"7HO-Tic", i.e., 7-hydroxy-1,2,3,4-tetrahydroisoquinoline-3-carboxylic acid, has the structure of:

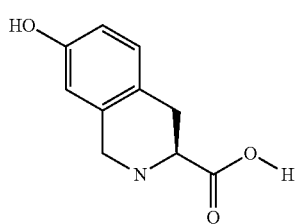 [SMILES: O=C(O)[C@@H]1Cc2ccc(O)cc2CN1]

"Tyr¹-Ψ-(CH₂—NH)" has the structure of:

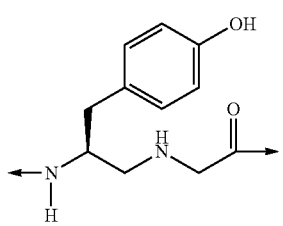

The Greek letter psi "Ψ" is used herein to indicate that a peptide bond has been replaced by a pseudopeptide bond. In an amino acid sequence name, the format of the Ψ term is A¹-Ψ-(X—X')A² wherein A¹ is the amino acyl radical whose carbonyl group has been modified to X and A² is the amino acyl radical whose α-amino group has been modified to X'. X and X' are shown as strings of element symbols separated by a bond, e.g., Tyr-Ψ-(CH₂—NH)Gly.

"Cys(succinimide-N-alkyl)" has the structure of:

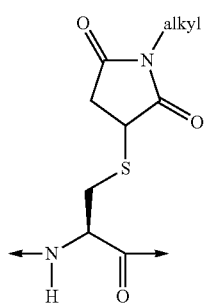

"Cys(Psu)" has the structure of:

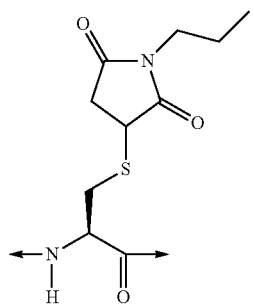

"Orn(N—C(O)—(CH₂)₁₂—CH₃)" has the structure of:

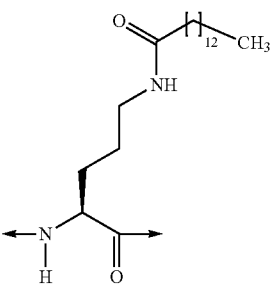

"Cys(succinimide-N—(CH₂)$_x$—C(O)—NH—(CH₂)$_y$—CH₃)" has the structure of:

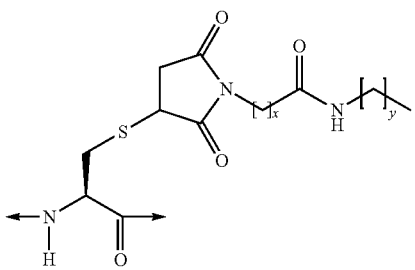

wherein, x=1-30, and y=1-30.

"hCys(succinimide-N—(CH₂)$_x$—C(O)—NH—(CH₂)$_y$—CH₃)" has the structure of:

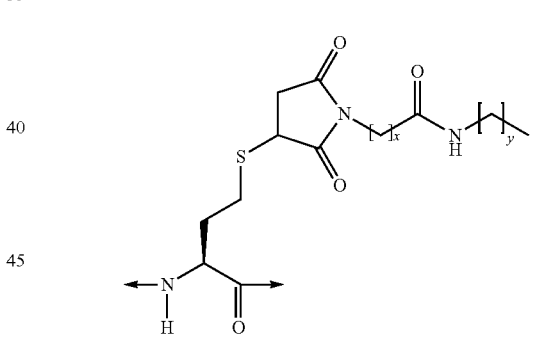

wherein, x=1-30, and y=1-30.

"Pen(succinimide-N—(CH₂)$_x$—C(O)—NH—(CH₂)$_y$—CH₃)" has the structure of:

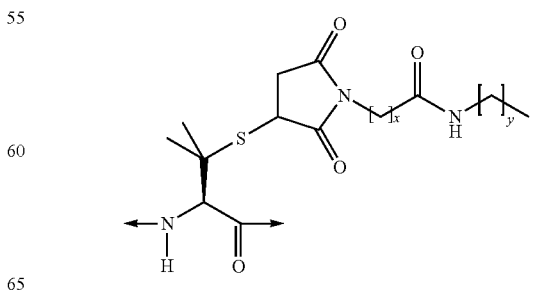

wherein, x=1-30, and y=1-30.

"Cys(succinimide-N—(CH$_2$)$_s$—NH—C(O)—(CH$_2$)$_t$—CH$_3$)" has the structure of:

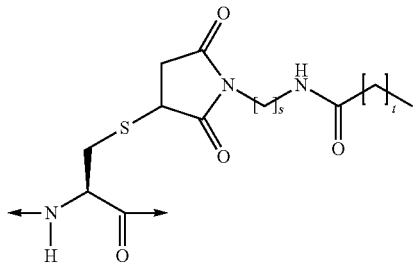

wherein, s=1-30, and t=1-30.

"hCys(succinimide-N—(CH$_2$)$_s$NH—C(O)—(CH$_2$)$_t$—CH$_3$)" has the structure of:

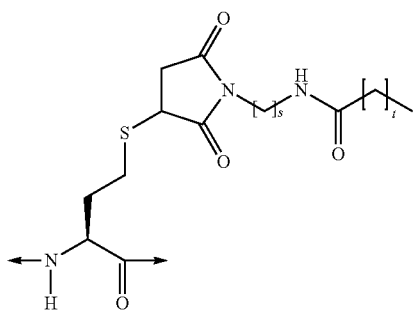

wherein s=1-30, and t=1-30.

"Pen(succinimide-N—(CH$_2$)$_s$—NH—C(O)—(CH$_2$)$_t$—CH$_3$)" has the structure of:

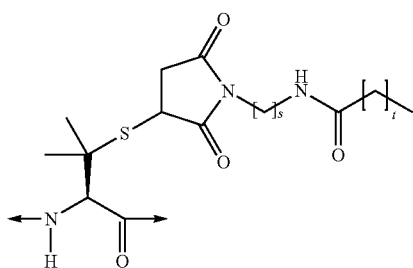

wherein s=1-30, and t=1-30.

"Cys(succinimide-N-PEG)" has the structure of:

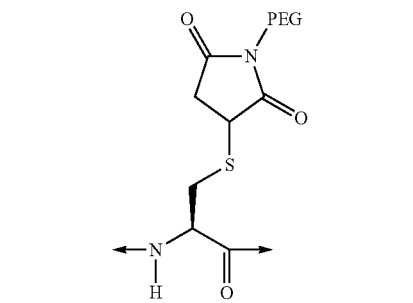

"hCys(succinimide-N-PEG)" has the structure of:

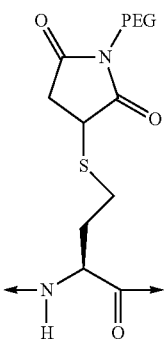

"Pen(succinimide-N-PEG)" has the structure of:

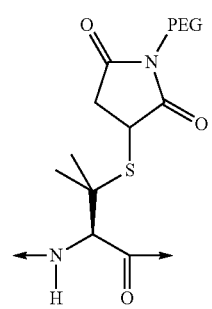

"Cys(succinimide-N—(CH$_2$)$_2$—C(O)NH—(CH$_2$)$_3$—PEG)" has the structure of:

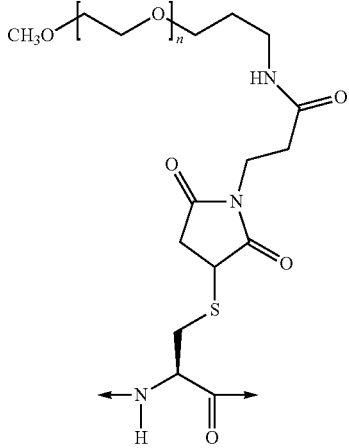

"Cys(succinimide-N—(CH$_2$)$_2$—C(O)NH—(CH$_2$)$_3$—O—CH$_2$—CH(PEG)-CH$_2$—PEG)" has the structure of:

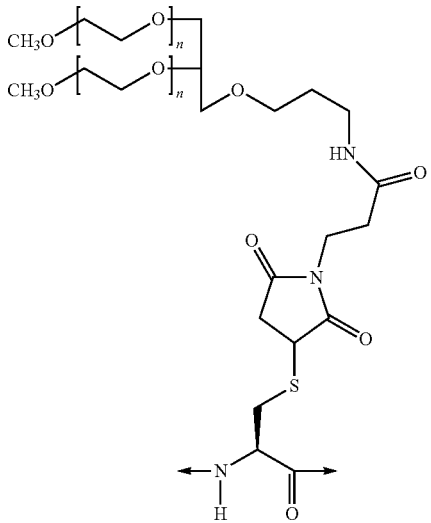

With the exception of the N-terminal amino acid, all abbreviations (e.g., Ala) of amino acids in this disclosure stand for the structure of —NH—C(R)(R')—CO—, wherein R and R' each is, independently, hydrogen or the side chain of an amino acid (e.g., R═CH$_3$ and R'═H for Ala), or R and R' may be joined to form a ring system. For the N-terminal amino acid, the abbreviation stands for the structure of (R$^2$R$^3$)N—C(R)(R')—CO—, wherein R$^2$ and R$^3$ are as defined in the above formula (I).

The term "(C$_1$-C$_{30}$)hydrocarbon moiety" encompasses alkyl, alkenyl and alkynyl, and in the case of alkenyl and alkynyl there are C$_2$-C$_{30}$.

A peptide of this invention is also denoted herein by another format, e.g., (A5c$^2$)hGIP(1-42)-OH (SEQ ID NO:3), with the substituted amino acids from the natural sequence placed between the brackets (e.g., A5c$^2$ for Ala$^2$ in hGIP). The numbers between the parentheses refer to the number of amino acids present in the peptide (e.g., hGIP(1-42)-OH (SEQ ID NO:1) is amino acids 1 through 42 of the peptide sequence for hGIP). The designation "NH$_2$" in hGIP(1-30)-NH$_2$ (SEQ ID NO:2) indicates that the C-terminus of the peptide is amidated; hGIP(1-42) (SEQ ID NO:1) or hGIP(1-42)-OH (SEQ ID NO:1) means that the C-terminus is the free acid.

Human GIP ("hGIP") has the amino acid sequence of:

```
                                              (SEQ ID NO: 1)
Tyr-Ala-Glu-Gly-Thr-Phe-Ile-Ser-Asp-Tyr-Ser-Ile-
1               5                   10

Ala-Met-Asp-Lys-Ile-His-Gln-Gln-Asp-Phe-Val-Asn-
        15                  20

Trp-Leu-Leu-Ala-Gln-Lys-Gly-Lys-Lys-Asn-Asp-Trp-
25              30                  35

Lys-His-Asn-Ile-Thr-Gln.
        40
```

"Acyl" refers to R"—C(O)—, where R" is H, alkyl, substituted alkyl, heteroalkyl, substituted heteroalkyl, alkenyl, substituted alkenyl, aryl, alkylaryl, or substituted alkylaryl.

"Alkyl" refers to a hydrocarbon group containing one or more carbon atoms, where multiple carbon atoms if present are joined by single bonds. The alkyl hydrocarbon group may be straight-chain or contain one or more branches or cyclic groups.

"Substituted alkyl" refers to an alkyl wherein one or more hydrogen atoms of the hydrocarbon group are replaced with one or more substituents selected from the group consisting of halogen, (i.e., fluorine, chlorine, bromine, and iodine), —OH, —CN, —SH, —NH$_2$, —NHCH$_3$, —NO$_2$, —C$_{1-20}$ alkyl substituted with halogens, —CF$_3$, —OCH$_3$, —OCF$_3$, and —(CH$_2$)$_{0-20}$—COOH. In different embodiments 1, 2, 3 or 4 substituents are present. The presence of —(CH$_2$)$_{0-20}$—COOH results in the production of an alkyl acid. Examples of alkyl acids containing, or consisting of, —(CH$_2$)$_{0-20}$—COOH include 2-norbornane acetic acid, tert-butyric acid and 3-cyclopentyl propionic acid.

"Heteroalkyl" refers to an alkyl wherein one of more of the carbon atoms in the hydrocarbon group are replaced with one or more of the following groups: amino, amido, —O—, —S— or carbonyl. In different embodiments 1 or 2 heteroatoms are present.

"Substituted heteroalkyl" refers to a heteroalkyl wherein one or more hydrogen atoms of the hydrocarbon group are replaced with one or more substituents selected from the group consisting of halogen, —OH, —CN, —SH, —NH$_2$, —NHCH$_3$, —NO$_2$, —C$_{1-20}$ alkyl substituted with halogens, —CF$_3$, —OCH$_3$, —OCF$_3$, and —(CH$_2$)$_{0-20}$—COOH. In different embodiments 1, 2, 3 or 4 substituents are present.

"Alkenyl" refers to a hydrocarbon group made up of two or more carbons wherein one or more carbon-carbon double bonds are present. The alkenyl hydrocarbon group may be straight-chain or contain one or more branches or cyclic groups.

"Substituted alkenyl" refers to an alkenyl wherein one or more hydrogens are replaced with one or more substituents selected from the group consisting of halogen, —OH, —CN, —SH, —NHCH$_3$, —NO$_2$, —C$_{1-20}$ alkyl substituted with halogens, —CF$_3$, —OCH$_3$, —OCF$_3$, and —(CH$_2$)$_{0-20}$—COOH. In different embodiments 1, 2, 3 or 4 substituents are present.

"Aryl" refers to an optionally substituted aromatic group with at least one ring having a conjugated pi-electron system, containing up to three conjugated or fused ring systems. Aryl includes carbocyclic aryl, heterocyclic aryl and biaryl groups. Preferably, the aryl is a 5 or 6 membered ring. Preferred atoms for a heterocyclic aryl are one or more sulfur, oxygen, and/or nitrogen. Examples of aryl include phenyl, 1-naphthyl, 2-naphthyl, indole, quinoline, 2-imidazole, and 9-anthracene. Aryl substituents are selected from the group consisting of —C$_{1-20}$ alkyl, —C$_{1-20}$ alkoxy, halogen, —OH, —CN, —SH, —NH$_2$, —NO$_2$, —C$_{1-20}$ alkyl substituted with halogens, —CF$_3$, —OCF$_3$, and —(CH$_2$)$_{0-20}$—COOH. In different embodiments the aryl contains 0, 1, 2, 3, or 4 substituents.

"Alkylaryl" refers to an "alkyl" joined to an "aryl".

Synthesis

The peptides of this invention can be prepared by standard solid phase peptide synthesis. See, e.g., Stewart, J. M., et al., 1984, Solid Phase Synthesis, Pierce Chemical Co., 2d ed. If R$^1$ is NH—X$^2$—CH$_2$—CONH$_2$, i.e., Z$^0$═CONH$_2$, the synthesis of the peptide starts with Fmoc-HN—X$^2$—CH$_2$—CONH$_2$ which is coupled to Rink amide MBHA resin. If R$^1$ is NH—X$^2$—CH$_2$—COOH, i.e., Z$^0$═COOH, the synthesis of the peptide starts with Fmoc-HN—X$^2$—CH$_2$—COOH which is coupled to Wang resin. For this particular step, 2 molar equivalents of Fmoc-HN—X$^2$—COOH, HBTU and HOBt and 10 molar equivalents of DIPEA are used. The coupling time is about 8 hours.

In the synthesis of a GIP analogue of this invention containing A5c, A6c, and/or Aib, the coupling time is 2 hrs for these residues and the residue immediately following them.

The substituents $R^2$ and $R^3$ of the above generic formula can be attached to the free amine of the N-terminal amino acid $A^1$ by standard methods known in the art. For example, alkyl groups, e.g., $(C_1$-$C_{30})$alkyl, can be attached using reductive alkylation. Hydroxyalkyl groups, e.g., $(C_1$-$C_{30})$hydroxyalkyl, can also be attached using reductive alkylation wherein the free hydroxy group is protected with a tert-butyl ester. Acyl groups, e.g., —C(O)$X^3$, can be attached by coupling the free acid, e.g., —$X^3$ COOH, to the free amine of the N-terminal amino acid by mixing the completed resin with 3 molar equivalents of both the free acid and diisopropylcarbodiimide in methylene chloride for about one hour. If the free acid contains a free hydroxy group, e.g., 3-fluoro-4-hydroxyphenylacetic acid, then the coupling should be performed with an additional 3 molar equivalents of HOBT.

The following examples describe synthetic methods for making a peptide of this invention, which methods are well-known to those skilled in the art. Other methods are also known to those skilled in the art. The examples are provided for the purpose of illustration and are not meant to limit the scope of the present invention in any manner.

Example 1

(4Hppa$^1$, Aib$^2$, A5c$^7$, Nle$^{14}$)hGIP(1-30)-NH$_2$

The titled peptide was automatically synthesized on an Applied Biosystems (Foster City, Calif., USA) model 433A peptide synthesizer based on fluorenylmethyloxycarbonyl (Fmoc) chemistry. Rink Amide MBHA (4-methylbenzhydrylamine) resin (Nova Biochem, La Jolla, Calif., USA) with substitution of 0.72 mmol/g was used. The Fmoc amino acid cartridges were from AnaSpec (San Jose, Calif., USA). The Fmoc amino acids with the side chain protections were as follows: Fmoc-Lys(Boc)-OH, Fmoc-Gln(Trt)-OH, Fmoc-Ala-OH, Fmoc-Leu-OH, Fmoc-Trp(Boc)-OH, Fmoc-Asn(Trt)-OH, Fmoc-Val-OH, Fmoc-Phe-OH, Fmoc-Asp(OtBu)-OH Fmoc-His(Trt)-OH, Fmoc-Ile-OH, Fmoc-Nle-OH, Fmoc-Ser(tBu)-OH, Fmoc-Tyr(tBu)-OH, Fmoc-A5C—OH, Fmoc-Thr(tBu)-OH, Fmoc-Gly-OH, and Fmoc-Glu(OtBu)-OH and Fmoc-Aib-OH. 3-(4-hydroxyphenyl)-propionic acid (4Hppa) was purchased from Sigma-Aldrich (St. Louis, Mo., USA). The synthesis was carried out on a 0.25 mmol scale. The ABI 433A peptide synthesizer was programmed to perform the following reaction cycle: (1) washing with NMP, (2) removing Fmoc protecting group with 20% piperidine in NMP for 10 minutes, (3) washing with NMP—during washing and removing of Fmoc cycles, the Fmoc amino acid (4 eq, 1 mmol) was first pre-activated with 2 ml solution of 0.45M 2-(1-H-benzotriazole-1-yl)-1,1,2,3-tetramethyluronium hexafluorophosphate/1-hydroxy-benzotriazole (HBTU/HOBT) in DMF; this activated amino acid ester, 1 ml of 2M diisopropylethyl amine (DIPEA) and 2.5 ml of NMP were added to the resin—and (4) coupling with pre-activated amino acid for 1 hr. The coupling of A5c with its following Phe and Aib with its following 4Hppa were prolonged to 3 hr. The resin was double coupled successively according to the sequence. After finishing the assembly of peptide chain, the protected peptide-resin was cleaved in a mixture of TFA, H$_2$O, TIS (15 ml/1.28 ml/1.35 ml) for 3 hr. It was filtered into 140 ml of cold ether and centrifuged to get precipitate. This crude product was dissolved in 20 ml of 50% AcOH and diluted with 180 ml water. It was purified on a reverse-phase preparative HPLC, using a column (4×43 cm) of C$_{18}$ DYNAMAX-100 A$^0$ (Varian, Walnut Creek, Calif., USA). The column was eluted with a linear gradient from 20% B to 45% B in 45 minutes, where A was 0.1% TFA in water and B was 0.1% TFA in CH$_3$CN. After being checked by MS and HPLC, all pure fractions were pooled and lyophilized to dryness. The purity of the compound was 99.90%. Electrospray ionization mass spectrometry (ESI-MS) analysis gave the molecular weight of 3510.8 in agreement with the calculated molecular weight of 3510.93.

Example 11

(3,5Br-Tyr$^1$, Aib$^{2, 13}$, Nle$^{14}$)hGIP(1-42)-OH

The titled peptide was automatically synthesized on an Applied Biosystems (Foster City, Calif., USA) model 433A peptide synthesizer based on fluorenylmethyloxycarbonyl (Fmoc) chemistry. Fmoc-Gln(Trt)-wang resin (Novabiochem., La Jolla, Calif., USA) with substitution of 0.59 mmol/g was used. The Fmoc amino acid cartridges were from AnaSpec (San Jose, Calif., USA). The Fmoc amino acids with the side chain protections were as follows: Fmoc-Thr(tBu)-OH, Fmoc-Ile-OH, Fmoc-Asn(Trt)-OH, Fmoc-His(Trt)-OH, Fmoc-Lys(Boc)-OH, Fmoc-Trp(Boc)-OH, Fmoc-Asp(OtBu)-OH, Fmoc-Gly-OH Fmoc-Gln(Trt)-OH, Fmoc-Ala-OH, Fmoc-Leu-OH, Fmoc-Val-OH, Fmoc-Phe-OH, Fmoc-Ile-OH, Fmoc-Nle-OH, Fmoc-Ser(tBu)-OH, Fmoc-Tyr(tBu)-OH, Fmoc-Glu(OtBu)-OH, and Fmoc-Aib-OH. 3,5Br-Tyr-OH was from Chem-Impex international (Wooddale, Ill., USA). The synthesis was carried out on a 0.25 mmol scale. The ABI 433A peptide synthesizer was programmed to perform the following reaction cycle: (1) washing with NMP, (2) removing Fmoc protecting group with 20% piperidine in NMP for 10 minutes, (3) washing with NMP—during the removing of Fmoc cycle and following washing, the Fmoc amino acid (4 eq., 1 mmol) was first pre-activated with 2 ml solution of 0.45M 2-(1-H-benzotriazole-1-yl)-1,1,2,3-tetramethyluronium hexafluorophosphate/1-hydroxy-benzotriazole (HBTU/HOBT) in DMF; this activated amino acid ester, 1 ml of 2M diisopropylethyl amine (DIPEA) and 2.5 ml of NMP were added to the resin—and (4) coupling with pre-activated amino acid for 1 hour. The coupling of Aib with its following Ile was prolonged to 3 hours. Coupling of 3,5Br-Tyr-OH was done manually with PYAOP [(7-azabenzotriazol-1-yl)oxytris (pyrrolidino) phosphonium hexafluorophosphate] as a coupling reagent in the presence of DIPEA and pentalfluorophenol. The resin was double coupled successively according to the sequence. After finishing the assembly of peptide chain, the protected peptide-resin was treated with a solution containing Na$_2$CO$_3$/DMF/DBU (1/0.5/0.1) for 2 hours, then cleaved Fmoc with 25% piperidine for 45 minutes. It was cleaved in a mixture of TFA, H$_2$O, TIS, thioanisole and phenol (12 ml/0.64/0.64/0.5/0.5) for 3 hours and then was filtered into 140 ml of cold ether. The precipitate was obtained after centrifugalization. This crude product was dissolved in 20 ml of 50% AcOH, diluted with 180 ml water and purified on a reverse-phase preparative HPLC, using a column (4×43 cm) of C$_{18}$ DYNAMAX-100 A$^0$ (Varian, Walnut Creek, Calif., USA). The column was eluted with a linear gradient from 20% B to 45% B in 45 minutes, where A was 0.1% TFA in water and B was 0.1% TFA in CH$_3$CN. After checked by MS and HPLC, all pure fractions were pooled and lyophilized to dryness. The purity was 99.90%. ESI mass analysis showed 5150.8.

Example 22

(3,4,5F-Phe$^1$, Aib$^2$, A5c$^{11}$, Nle$^{14}$)hGIP(1-42)-OH

Side chain protected Fmoc-[Aib$^2$, A5c$^{11}$, Nle$^{14}$]hGIP(2-42)-Wang resin was synthesized on an Applied Biosystems model 433A peptide synthesizer (Foster City, Calif., USA) using fluorenylmethyloxycarbonyl (Fmoc) chemistry. A Fmoc-Gln(Trt)-Wang Resin (Novabiochem., San Diego, Calif., USA) with substitution of 0.59 mmol/g was used. The Fmoc amino acids (AnaSpec, San Jose, Calif., USA) used were Fmoc-Ala-OH, Fmoc-Aib-OH, Fmoc-Asn(Trt)-OH, Fmoc-Asp(tBu)-OH, Fmoc-A5c-OH, Fmoc-Gln(Trt)-OH, Fmoc-Glu(tBu)-OH, Fmoc-Gly-OH, Fmoc-His(Trt)-OH, Fmoc-Ile-OH, Fmoc-Leu-OH, Fmoc-Lys(Boc)-OH, Fmoc-Phe-OH-Fmoc-Nle-OH, Fmoc-Ser(tBu)-OH, Fmoc-Tyr(tBu)-OH, Fmoc-Thr(tBu)-OH, Fmoc-Trp(Boc)-OH, and Fmoc-Val-OH. The synthesis was carried out on a 0.2 mmol scale. The Fmoc groups were removed by treatment with 20% piperidine in N-methylpyrrolidone (NMP) for 30 minutes. In each coupling step, the Fmoc amino acid (3 eq., 0.3 mmol) was first pre-activated in 2 ml solution of 0.45M 2-(1-H-benzotriazole-1-yl)-1,1,2,3-tetramethyluronium hexafluorophosphate/1-hydroxy-benzotriazole (HBTU/HOBT) in NMP. This activated amino acid ester, 1 ml of diisopropylethyl amine (DIPEA) and 1 ml of NMP were added to the resin. The ABI 433A peptide synthesizer was programmed to perform the following reaction cycle: (1) washing with NMP, (2) removing Fmoc protecting group with 20% piperidine in NMP for 30 minutes, (3) washing with NMP, (4) coupling with pre-activated Fmoc amino acid for 3 hours, (5) washing with NMP, and (6) coupling with pre-activated Fmoc amino acid for 3 hours. One equivalent of TFFH (tetramethylfluoroformamidinium hexafluorophosphate; Perceptive Biosystems, Warrington, UK) was added to the coupling of Fmoc-A5c-OH and Fmoc-Tyr(tBu)-OH in positions 10 and 11. The resin was double coupled successively according to the sequence of the title peptide. After the peptide chain was assembled the resin was washed completely by using N,N-dimethylformamide (DMF) and dichloromethane (DCM).

At the end of the assembly of the peptide chain on the 433A, the peptide-resin was transferred to a reaction vessel on a shaker and the Fmoc was removed using 25% Pip/DMF for 30 minutes. The resin was washed with DMF. Fmoc-Phe (3,4,5-F)-OH (1.0 mmole) was coupled using PyAOP(1(7-Azabenzotriazol-1-yloxytris(pyrrolidino)phosphonium-hexafluorophosphate, Applied Biosystems, 6 mmole), Pentafluorophenol (Oakwood Products; West Columbia, S.C., USA) (2.0 mmole) and DIPEA (2.0 mmole). The Fmoc group was removed as above.

To cleave the title peptide, resin was treated with a mixture of TFA, H$_2$O and triisopropylsilane (TIS) (9.5 ml/0.85 ml/0.8 ml) for 4 hours. The resin was filtered off and the filtrate was poured into 200 ml of ether. The precipitate was collected by centrifugation. This crude product was dissolved in a mixture of acetonitrile and water and purified on a reverse-phase preparative HPLC system with a column (250-21.2 mm) of C$_{18}$ Luna (Phenomenex). The column was eluted over 80 minutes using a linear gradient of 100% A:to 55% A:45% B, where A was 0.1% TFA in water and B was 0.1% TFA in acetonitrile. The fractions were checked by analytical HPLC and those containing pure product were pooled and lyophilized to dryness to give 156.5 mg (15.5%) of a white solid. Purity was assayed using HPLC and found to be approximately 99.90%. Electrospray ionization mass spectrometry (ESI-MS) analysis gave the molecular weight at 5041.5.

Example 40

[Tyr$^1$Ψ(CH$_2$NH)Gly$^2$, A5c$^{11, 41}$]hGIP(1-42)-OH

A. Assembly of Peptide Chain of (Gly$^2$, A5c$^{11, 41}$)hGIP(2-42)-OH

It was assembled using microwave-assisted Fmoc Chemistry on a Liberty Peptide Synthesizer (CEM; Matthews, N.C., USA) at the 0.20 mmole scale. Pre-loaded Fmoc-Gln (Trt)-Wang resin (0.59 mmole/g; Novabiochem, San Diego, Calif., USA) was used to generate the C-terminal acid peptide. The resin (0.423 g) was placed in a 50 ml conical tube along with 15 ml of dimethylformamide (DMF) and loaded onto a resin position on the synthesizer. The resin was then quantitatively transferred to the reaction vessel via the automated process. The standard Liberty synthesis protocol for 0.25 mmole scale synthesis was used. This protocol involves deprotecting the N-terminal Fmoc moiety via an initial treatment with 7 ml of 20% piperidine, containing 0.1M N-hydroxybenzotriazole (HOBT), in DMF. The initial deprotection step was for 30 seconds with microwave power (45 watts, maximum temperature of 75° C.), and nitrogen bubbling (3 seconds on/7 seconds off). The reaction vessel was then drained and a second piperidine treatment, identical to the first treatment, except that it was for a 3-minute duration. The resin was then drained and thoroughly washed with DMF several times. Cycle 2 was coupling of Fmoc-A5c-OH, its 0.2M stock solution in DMF was then added (2.5 ml, 5 eq.), followed by 1.0 ml of 0.45M (4.5 eq.) HBTU [2-(1H-benzotriazole-1-yl)-1,1,3,3-tetramethyluronium hexafluorophosaphate] in DMF. This was followed by the addition of 0.5 ml of 2M (10 eq.) DIPEA (diisopropylethyl amine) in NMP(N-methylpyrrollidinone). The coupling step was performed for 5 minutes using 20 watts of microwave power at a max temperature of 75° C. and the same rate of nitrogen bubbling. Following the initial coupling step the reaction vessel was drained to waste and the coupling was repeated once. Cycle 3 following Fmoc A5c was used aggressive coupling in which coupling step was performed for 10 minutes using 20 watts of microwave power at a max temperature of 90° C. All amino acids were introduced similarly to those described at cycle 2 except that aggressive couplings were applied to Fmoc A5c-OH at Cycle 32 and its following Fmoc Tyr(tBu)-OH. A double-coupling strategy was employed throughout the entire sequence. Cycles 2, 4, 20, 21, 26, 27, 31, 36 37, 38, 39, 41 contained a capping procedure immediately following the coupling step. Capping was performed by adding 7 mL of 0.5M acetic anhydride, containing 0.015M HOBT in NMP, along with 2 mL of the 2M DIPEA solution using a multi-step microwave protocol: 50 watts of power for 30 seconds (65° C. max temperature), followed by 30 seconds of microwave power off, followed by a second round of 30 seconds of microwave power on (50 watts), and then again 30 seconds of no microwave power. The resin was then drained and thoroughly washed with DMF. The following amino acids (Advanced Chemtech, Louisville, Ky., USA) were used: Cycle 2: Fmoc-A5c-OH; Cycle 3: Fmoc-Ile-OH; Cycle 4: Fmoc-Asn (Trt)-OH; Cycle 5: Fmoc-His(Trt)-OH; Cycle 6: Fmoc-Lys (Boc)-OH; Cycle 7: Fmoc-Trp(Boc)-OH; Cycle 8: Fmoc-Asp(OtBu)-OH; Cycle 9: Fmoc-Asn(Trt)-OH; Cycle 10: Fmoc-Lys(Boc)-OH; Cycle 11: Fmoc-Lys(Boc)-OH; Cycle 12: Fmoc-Gly-OH; Cycle 13: Fmoc-Lys(Boc)-OH; Cycle 14: Fmoc-Gln(Trt)-OH; Cycle 15: Fmoc-Ala-OH; Cycle 16: Fmoc-Leu-OH; Cycle 17: Fmoc-Leu-OH; Cycle 18: Fmoc- Trp(Boc)-OH; Cycle 19: Fmoc-Asn(Trt)-OH; Cycle 20: Fmoc-Val-OH; Cycle 21: Fmoc-Phe-OH; Cycle 22: Fmoc-Asp(OtBu)-OH; Cycle 23: Fmoc-Gln(Trt)-OH; Cycle 24: Fmoc-Gln(Trt)-OH; Cycle 25: Fmoc-His(Trt)-OH; Cycle 26: Fmoc-Ile-OH; Cycle 27: Fmoc-Lys(Boc)-OH; Cycle 28: Fmoc-Asp(OtBu)-OH; Cycle 29: Fmoc-Met-OH; Cycle 30: Fmoc-Ala-OH; Cycle 31: Fmoc-Ile-OH; Cycle 32:Fmoc-A5C—OH, Cycle 33: Fmoc-Tyr(tBu)-OH, Cycle 34: Fmoc-Asp(OtBu)-OH; Cycle 35: Fmoc-Ser(tBu)-OH; Cycle 36: Fmoc-Ile-OH; Cycle 37: Fmoc-Phe-OH; Cycle 38: Fmoc-Thr(oBu))-OH; Cycle 39: Fmoc-Gly-OH, Cycle 40: Fmoc-Glu(OtBu)-OH, and Cycle 41: Fmoc-Gly-OH. The coupling protocol for Fmoc-His(Trt)-OH was a slightly modified version of the standard protocol. The microwave power was off for the first 2 minutes, followed by 4 minutes with microwave power on (20 watts; max temperature of 50° C.). After assembly of peptide chain was finished, the resin was treated with 20% piperidine in DMF for 40 minutes to deprotect Fmoc at N-terminal.

B. Synthesis of Fmoc-Tyr(tBu)-CHO

Fmoc-Tyr(tBu)-OH was converted to N-methoxy-N-methyl-α-(Fmoc-Tyr(tBu)-carboxamide. Fmoc-Tyr(tBu)-OH (4.6 g, 10 mmol) in 100 ml DCM was mixed with O,N-dimethylhydroxylamine hydrochloride (1 g, 10 mmol), HOBT (1.37 g, 10.1 mmol, and DIPEA (5.25 ml, 30 mmol) at ice bath for 15 minutes, to which EDC (2.11 g, 11 mmol) was added. The reaction solution was stirred at room temperature for 15 hrs. It was diluted with DCM, which was successively washed by sat. $NaHCO_3$ (50 ml×3), 10% citric acid (50 ml×3) and brine (50 ml×3). After all DCM layer was dried over $MgSO_4$, it was stripped down to give 4.62 g with MS 503.4 (MW 503.6).

N-methoxy-N-methyl-α-(Fmoc-Tyr(tBu)-carboxamide was reduced to Fmoc-Tyr(tBu)-CHO. Lithium aluminum hydride (36 ml, 1M) was slowly added to a cooled 60 ml stirred THF solution of N-methoxy-N-methyl-α-(Fmoc-Tyr (tBu)-carboxamide (3.6 g, 7.1 mmol) in 50 minutes. The reduction was finished in 20 minutes. The mixture was hydrolyzed with 100 ml of 0.5 N $KHSO_4$ for 0.5 hr. It was extracted with 200 ml ether. All organic layer was washed with 10% $KHSO_4$ (50 ml×2), brine (50 ml×3) then dried over $MgSO_4$. The solvent was evaporated to give crude aldehyde product.

The above crude Fmoc-Tyr(tBu)-CHO (3.115 mmol) in 5 ml DMF was added into peptide (Gly[2], A5c[11,41])hGIP(2-42)-resin (0.2 mmol) containing 5 ml DMF with 100 μl AcOH. It was treated with $NaBH_3CN$ (0.1957 g) for 1 hr, then second portion of $NaBH_3CN$ (0.1957 g) was added. It was repeated once again, then the resin was shaken overnight. After the resin was washed and cleaved Fmoc with 25% piperidine for 45 minutes. It was cleaved with a solution of TFA, $H_2O$, TI and DTT (15 ml/1.28 ml/1.35 ml/0.75 g) for 3 hr and then was filtered into 140 ml of cold ether. The precipitate was obtained after centrifugalization. This crude product was dissolved in 20 ml of 50% AcOH, diluted with 180 ml water and purified on a reverse-phase preparative HPLC, using a column (4×43 cm) of $C_{18}$ DYNAMAX-100 A⁰ (Varian, Walnut Creek, Calif., USA). The column was eluted with a linear gradient from 20% B to 45% B in 45 minutes, where A was 0.1% TFA in water and B was 0.1% TFA in $CH_3CN$. After checked by MS and HPLC, all pure fractions were pooled and lyophilized to dryness. The purity was 98.93%. ESI mass analysis showed 4989.7 in agreement with the calculated molecular weight of 4989.67.

Other peptides of the invention can be prepared by a person of ordinary skill in the art using synthetic procedures analogous to those disclosed in the foregoing examples. Physical data for the compounds exemplified herein are given in Table 1.

TABLE 1

| Example Number | Mol. Wt. (Expected) | Mol. Wt. (ESI-MS) | % Purity (HPLC) |
|---|---|---|---|
| 1 | 3510.93 | 3510.8 | 99.90 |
| 2 | 3510.98 | 3510.8 | 99.90 |
| 3 | 3528.97 | 3529.1 | 98.30 |
| 4 | 3529.02 | 3528.6 | 95.40 |
| 5 | 3512.95 | 3512.4 | 96.90 |
| 6 | 3530.99 | 3530.5 | 99.90 |
| 7 | 4964.57 | 4964.5 | 99.90 |
| 8 | 4962.60 | 4963.3 | 99.90 |
| 9 | 3480.95 | 3481.3 | 95.00 |
| 10 | 4967.56 | 4967.4 | 99.90 |
| 11 | 5151.38 | 5150.8 | 99.90 |
| 12 | 4977.60 | 4977.8 | 99.90 |
| 13 | 5161.42 | 5161.3 | 99.90 |
| 14 | 5038.07 | 5038.6 | 99.90 |
| 15 | 5082.53 | 5082.5 | 99.90 |
| 16 | 5129.52 | 5129.7 | 99.90 |
| 17 | 5255.41 | 5255.7 | 99.90 |
| 18 | 5002.65 | 5003.0 | 99.90 |
| 19 | 5017.66 | 5018.3 | 99.00 |
| 20 | 5022.8 | 5022.2 | 99.00 |
| 21 | 5016.67 | 5016.3 | 99.90 |
| 22 | 5041.60 | 5041.5 | 99.90 |
| 23 | 5005.62 | 5005.7 | 99.90 |
| 24 | 5023.61 | 5023.7 | 99.90 |
| 25 | 5023.61 | 5023.7 | 99.90 |
| 26 | 5031.71 | 5032.3 | 95.10 |
| 27 | 5047.71 | 5048.4 | 99.90 |
| 28 | 5061.73 | 5062.3 | 98.30 |
| 29 | 5073.74 | 5074.2 | 96.00 |
| 30 | 5059.76 | 5059.8 | 99.90 |
| 31 | 5045.73 | 5046.6 | 97.50 |
| 32 | 5033.70 | 5034.2 | 98.70 |
| 33 | 5016.70 | 5017.5 | 99.70 |
| 34 | 5016.70 | 5017.3 | 99.20 |
| 35 | 5022.72 | 5023.7 | 99.90 |
| 36 | 5076.70 | 5077.5 | 97.10 |
| 37 | 5021.74 | 5022.7 | 99.90 |
| 38 | 5040.72 | 5041.3 | 96.40 |
| 39 | 5009.59 | 5009.5 | 95.14 |
| 40 | 4989.67 | 4989.7 | 98.93 |
| 41 | 5033.70 | 5033.9 | 99.40 |
| 53 | 5186.9 | 5187.7 | 98.7 |
| 54 | 5166.8 | 5166.9 | 99.9 |
| 55 | 5168.8 | 5169.2 | 99.9 |
| 61 | 5161.2 | 5161.7 | 99.9 |
| 62 | 5159.2 | 5159.5 | 99.9 |
| 63 | 5173.2 | 5173.8 | 96.5 |
| 64 | 5175.2 | 5176.1 | 99.9 |
| 71 | 5219.7 | 5219.7 | 95.6 |
| 72 | 5217.7 | 5217.7 | 95.4 |
| 73 | 5188.8 | 5188.9 | 95.3 |
| 74 | 5168.8 | 5168.9 | 99.9 |
| 75 | 5178.8 | 5178.9 | 99.9 |
| 77 | 5170.8 | 5171.4 | 98.4 |
| 78 | 5156.8 | 5157.3 | 96.8 |
| 79 | 5167.8 | 5167.7 | 99.1 |
| 80 | 5172.8 | 5172.4 | 98.8 |
| 81 | 5334.5 | 5334.7 | 99.9 |
| 82 | 5332.5 | 5333.1 | 99.9 |
| 83 | 5348.6 | 5348.9 | 99.9 |
| 85 | 5140.2 | 5140.7 | 99.9 |
| 86 | 5224.3 | 5224.6 | 99.9 |
| 87 | 5222.2 | 5223.5 | 99.9 |
| 88 | 26364 | 26367 | 99.6 |
| 89 | 35703 | 35706 | 99.9 |
| 102 | 48112 | 48132 | 99.9 |

Functional Assays

A. In Vitro hGIP Receptor Binding Assay

Membranes for in vitro receptor binding assays were prepared by homogenizing the CHO-K1 clonal cells expressing the human recombinant GIP receptor, with a Brinkman Polytron (setting 6, 15 sec), in ice-cold 50 mM Tris-HCl and then subjected to two centrifugations at 39,000 g for 10 minutes, with a resuspension in fresh buffer in between. For the assay, aliquots of the washed membrane preparations were incubated (100 minutes at 25° C. with 0.05 nM [$^{125}$I]GIP (~2200 Ci/mmol) in 50 mM Tris-HCl, 0.1 mg/ml bacitracin, and 0.1% BSA. The final assay volume was 0.5 ml. The incubations were terminated by rapid filtration through GF/C filters (pre-soaked in 0.5% polyethylenimine) using a Brandel filtration manifold. Each tube and filter were then washed three times with 5-ml aliquots of ice-cold buffer.

Specific binding was defined as the total radioligand bound minus that bound in the presence of 1000 nM GIP. In vitro hGIP receptor binding data for the compounds exemplified herein are given in Table 2.

B. Human and Rat Plasma Half-Life Assay

GIP peptide (50 µl 1 mg/ml) was added to 450 µl plasma (human or rat), vertexed briefly and incubated at 37° C. 50 µl was removed at various times, like at 0, 1, 2, 3, 4, 8, 24, 32, 48, 56, 72 hours, mixed with 5 µl formic acid and 150 µL acetonitrile in a microcentrifuge tube, vertexed, and centrifuged for 10 minutes at 10 K rpm. The supernatant was transferred to an injection vial and analyzed by LC-MS. The LC-MS system consisted of an API4000 mass spectrometer with an ESI probe. Positive ion mode and full scan detection were used. HPLC separation was carried out on a Luna 3µ. C8 (2), 2×30 mm column with a gradient from 90% A to 90% B in 10 minutes at a flow rate of 0.3 ml/min. Buffer A was 1% formic acid in water and buffer B was 1% formic acid acetonitrile. Human and rat plasma half-life data for the compounds exemplified herein are given in Table 2.

TABLE 2

| Example Number | Ki (nM) | Human Plasma T½ (hr) | Rat Plasma T½ (hr) |
| --- | --- | --- | --- |
| 1 | 12.58 | N/A | N/A |
| 2 | 20.31 | N/A | N/A |
| 3 | 5.00 | N/A | N/A |
| 4 | 15.43 | N/A | N/A |
| 5 | 2.95 | 50.6 | 83.5 |
| 6 | 1.58 | N/A | N/A |
| 7 | 250.52 | 38.5 | 6.8 |
| 8 | 706.61 | >53 | 12.9 |
| 9 | N/A | 26.5 | 14.0 |
| 10 | 3.33 | 71.4 | 9.2 |
| 11 | 4.26 | 30.0 | 11.8 |
| 12 | 3.18 | 82.5 | 11.0 |
| 13 | 21.76 | 50.6 | 13.1 |
| 14 | 0.42 | 52.1 | 27.4 |
| 15 | 0.60 | 50.6 | 22.9 |
| 16 | 5.03 | 52.1 | 18.5 |
| 17 | 77.91 | >72 | 30.1 |
| 18 | 3.40 | >72 | 32.1 |
| 19 | 77.29 | >72 | 15.2 |
| 20 | 9.40 | >74 | 24.3 |
| 21 | 95.00 | >74 | 6.0 |
| 22 | 31.12 | >74 | 69.3 |
| 23 | 2.70 | >74 | >74 |
| 24 | 15.67 | >74 | >74 |
| 25 | 26.00 | >74 | >74 |
| 26 | 7.52 | 26.2 | 48.8 |
| 27 | 6.69 | 7.0 | 5.1 |
| 28 | 1.24 | >57 | 10.03 |
| 29 | 0.73 | 29.5 | 18.9 |
| 30 | 1.03 | 27.6 | 7.2 |
| 31 | 4.50 | 34.8 | 9.7 |
| 32 | 5.82 | 23.9 | >61 |
| 33 | 8.14 | 32.8 | 15.5 |
| 34 | 9.75 | >63 | 16.3 |
| 35 | 3.28 | 74.5 | 50.6 |
| 36 | 11.24 | >72 | 11.7 |
| 37 | 7.05 | 29.3 | >72 |
| 38 | 14.44 | 16.4 | >72 |
| 39 | 10.41 | >72 | >72 |
| 40 | 48.96 | >48 | 11.9 |
| 41 | 5.43 | 63.6 | >66 |
| 53 | 34.99 | 20.0 | 23.2 |
| 54 | 50.17 | >50 | 21.5 |
| 55 | 39.04 | 37.7 | 16.1 |
| 61 | 8.89 | 34.7 | 8.2 |
| 62 | 5.06 | 41.7 | 11.1 |
| 63 | 0.78 | 43.0 | 34.7 |
| 64 | 0.76 | N/A | N/A |
| 71 | 1.09 | N/A | N/A |
| 72 | 0.92 | N/A | N/A |
| 73 | 3.90 | 28.6 | 11.8 |
| 74 | 9.34 | >50 | 12.8 |
| 75 | 6.40 | >60 | 18.6 |
| 77 | 4.82 | N/A | N/A |
| 78 | 9.13 | 14.9 | >52 |
| 79 | 5.12 | 26.3 | 21.7 |
| 80 | 9.42 | 22.6 | 18.4 |
| 81 | 6.64 | N/A | N/A |
| 82 | 9.06 | N/A | N/A |
| 83 | N/A | N/A | N/A |
| 85 | 0.83 | 9.4 | 11.5 |
| 86 | 9.13 | N/A | N/A |
| 87 | 1.41 | N/A | N/A |
| 102 | 42.37 | N/A | N/A |

C. Determination of Cyclic AMP Stimulation

1×105 CHO-K$_1$ cells expressing the human recombinant GIP receptor or RIN-5F insulinoma cells were seeded overnight into 24-well cell culture plates (Corning Incorporate, Corning, N.Y., USA). For the assay, the cells were preincubated in 500 µl of Hanks balanced salt solution (Sigma, St. Louis, Mo., USA) with 0.55 mM IBMX (Sigma, St. Louis, Mo., USA) adjusted to pH 7.3 for 10 minutes. GIP or its analogs was then added at a concentration of 100 nM. Following a 30-minute incubation at 37° C., the plates were placed on ice and 500 µl of ice-cold absolute ethanol was added to stop the reaction. The contents of the wells were collected, spun at 2,700 g for 20 minutes at 4° C. to remove cellular debris. The cAMP levels in the supernatants were determined by radioimmunoassay (New England Nuclear, Boston, Mass., USA).

D. Determination of in vivo Insulin Secretion in Normal Rats

Male Sprague Dawley rats with a body weight of approximately 275-300 g were used as experimental subjects. The day prior to the treatment, right atrial cannulae were implanted via the jugular vein under chlorohydrate. Each cannula was filled with 100 u/ml heparin saline and tied. The rats were fasted for approximately 18 hours prior to dosing with the compound or the vehicle (saline/0.25% BSA). The day of the experiment, aliquots of compound were thawed, brought to room temperature and vortexed thoroughly. A careful check was made for any sign of compound coming out of solution. 10 minutes prior to compound/glucose injection, a 500 µl blood sample was withdrawn and replaced with an equal volume of heparinized saline (10 u/ml). At time 0, a 500 µl blood sample was withdrawn through the cannula. Next, either the vehicle or the appropriate dose of the compound was injected into the cannula and pushed in with the glucose (1 g/kg) or vehicle solution. Finally, 500 µl of volume of heparinized saline (10 u/ml) was used to push in the remaining glucose through the cannula. Additional 500 µl blood samples were withdrawn at 2.5, 5, 10, and 20-minute post-glucose dosing; each immediately followed by a bolus, iv injection of 500 µl heparinized saline (10 u/ml) through the cannula. The plasma was collected from the blood samples by centrifugation, and stored at −20° C. until assay for insulin content. Numerical values of the total insulin secretion, which show the in vivo effects of the compounds of Examples 14 and 28, are summarized in Table 3.

TABLE 3

|  | AUC |
|---|---|
| Vehicle/Vehicle | 20.54 |
| Vehicle/Glucose | 4.11 |
| Example 14 | 189.54 |
| Example 28 | 92.88 |

Administration

The peptides of this invention can be provided in the form of pharmaceutically acceptable salts. Examples of such salts include, but are not limited to, those formed with organic acids (e.g., acetic, lactic, maleic, citric, malic, ascorbic, succinic, benzoic, methanesulfonic, toluenesulfonic, or pamoic acid), inorganic acids (e.g., hydrochloric acid, sulfuric acid, or phosphoric acid), and polymeric acids (e.g., tannic acid, carboxymethyl cellulose, polylactic, polyglycolic, or copolymers of polylactic-glycolic acids). A typical method of making a salt of a peptide of the present invention is well known in the art and can be accomplished by standard methods of salt exchange. Accordingly, the TFA salt of a peptide of the present invention (the TFA salt results from the purification of the peptide by using preparative HPLC, eluting with TFA containing buffer solutions) can be converted into another salt, such as an acetate salt by dissolving the peptide in a small amount of 0.25 N acetic acid aqueous solution. The resulting solution is applied to a semi-prep HPLC column (Zorbax, 300 SB, C-8). The column is eluted with (1) 0.1N ammonium acetate aqueous solution for 0.5 hrs, (2) 0.25N acetic acid aqueous solution for 0.5 hrs, and (3) a linear gradient (20% to 100% of solution B over 30 minutes) at a flow rate of 4 ml/min (solution A is 0.25N acetic acid aqueous solution; solution B is 0.25N acetic acid in acetonitrile/water, 80:20). The fractions containing the peptide are collected and lyophilized to dryness.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. In general, an effective dosage for the activities of this invention is in the range of $1 \times 10^{-7}$ to 200 mg/kg/day, preferably $1 \times 10^{-4}$ to 100 mg/kg/day, which can be administered as a single dose or divided into multiple doses.

The compounds of this invention can be administered by oral, parenteral (e.g., intramuscular, intraperitoneal, intravenous or subcutaneous injection, or implant), nasal, vaginal, rectal, sublingual, or topical routes of administration, and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include, without limitation, pharmaceutically acceptable emulsions, solutions, suspensions, syrups, elixirs, and the like, containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include, without limitation, sterile aqueous or non-aqueous solutions, suspensions, emulsions, and the like. Examples of non-aqueous solvents or vehicles include propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

Further, a compound of this invention can be administered in a sustained release composition such as those described in the following patents and patent applications. U.S. Pat. No. 5,672,659 teaches sustained release compositions comprising a bioactive agent and a polyester. U.S. Pat. No. 5,595,760 teaches sustained release compositions comprising a bioactive agent in a gelable form. U.S. Pat. No. 5,821,221 teaches polymeric sustained release compositions comprising a bioactive agent and chitosan. U.S. Pat. No. 5,916,883 teaches sustained release compositions comprising a bioactive agent and cyclodextrin. PCT Pub. No. WO99/38536 teaches absorbable sustained release compositions of a bioactive agent. PCT Pub. No. WO00/04916 teaches a process for making microparticles comprising a therapeutic agent such as a peptide in an oil-in-water process. PCT Pub. No. WO00/09166 teaches complexes comprising a therapeutic agent such as a peptide and a phosphorylated polymer. PCT Pub. No. WO00/25826 teaches complexes comprising a therapeutic agent such as a peptide and a polymer bearing a non-polymerizable lactone.

Unless defined otherwise, all technical and scientific terms used herein have the same meaning as commonly understood by one of ordinary skill in the art to which this invention belongs. Also, all publications, patent applications, patents and other references mentioned herein are hereby incorporated by reference, each in its entirety.

What is claimed is:

1. A compound of formula (I),

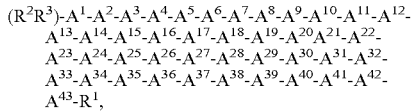

wherein:

$A^1$ is Cpa, His, 4Hppa, 2-Pal, 3-Pal, 4-Pal, 3Br-Phe, 4CF$_3$-Phe, 3Cl-Phe, 4CN-Phe, 3F-Phe, 4F-Phe, 3,4F-Phe, 3,5F-Phe, 3,4,5F-Phe, 4Me-Phe, 4NH$_2$-Phe, 4NH$_2$CH$_2$-Phe, 3OH-Phe, Taz, 3Thi, 7HO-Tic, Tyr(Ac), Tyr(Me), β-Tyr, 3Br-Tyr, 3,5Br-Tyr, 3Cl-Tyr, 2F-Tyr, 3F-Tyr, hTyr, 3I-Tyr, 3,5I-Tyr, αMe-Tyr, 2,6Me-Tyr, 3MeO-Tyr, 3NH$_2$-Tyr, 3NO$_2$-Tyr, 3OH-Tyr, or 3(HO—CH$_2$)Tyr;

$A^2$ is Ala, Abu, D-Abu, Acc, Aib, β-Ala, D-Ala, Gaba, Gly, Ser, D-Ser, Thr, D-Thr, Val, or D-Val;

$A^3$ is Glu, Aib, Asp, N-Me-Asp, Dhp, Dmt, N-Me-Glu, 3Hyp, 4Hyp, 4Ktp, Pro, hPro, Thz, or Tic;

$A^4$ is Gly, Acc, Aib, or β-Ala;

$A^5$ is Thr, Acc, Aib, or Ser;

$A^6$ is Phe, Acc, Aib, Aic, Cha, 1Nal, 2Nal, 2-Pal, 3-Pal, 4-Pal, ($X^4$, $X^5$, $X^6$, $X^7$, $X^8$)Phe, or Trp;

$A^7$ is Ile, Abu, Acc, Aib, Ala, Cha, Leu, Nle, Phe, Tle, or Val;

$A^8$ is Ser, Aib, or Thr;

$A^9$ is Asp, Aib, or Glu;

$A^{10}$ is Tyr, Acc, Cha, 1Nal, 2Nal, 2-Pal, 3-Pal, 4-Pal, Phe, or ($X^4$, $X^5$, $X^6$, $X^7$, $X^8$)Phe;

$A^{11}$ is Ser, Acc, Aib, Nle, or Thr;

$A^{12}$ is Ile, Abu, Acc, Aib, Ala, Cha, Leu, Nle, Phe, Tle, or Val;

$A^{13}$ is Ala, Acc, Aib, p-Ala, D-Ala, Gly, or Ser;

$A^{14}$ is Met, Abu, Acc, Aib, Ala, Cha, Ile, Leu, Nle, Phe, Tle, or Val;

$A^{15}$ is Asp, Aib, or Glu;

$A^{16}$ is Lys, Amp, Apc, Arg, hArg, Orn, HN—CH(($CH_2$)$_n$—N($R^4R^5$))—C(O), Cys(succinimide-N-alkyl), hCys(succinimide-N-alkyl), Pen(succinimide-N-alkyl), Cys(succinimide-N—($CH_2$)$_x$—C(O)—NH—($CH_2$)$_y$—$CH_3$), hCys(succinimide-N—($CH_2$)$_x$—C(O)—NH—($CH_2$)$_y$—$CH_3$), Pen(succinimide-N—($CH_2$)$_x$—C(O)—NH—($CH_2$)$_y$—$CH_3$), Cys(succinimide-N—($CH_2$)$_s$—NH—C(O)—($CH_2$)$_t$—$CH_3$), hCys(succinimide-N—($CH_2$)$_s$—NH—C(O)—($CH_2$)$_t$—$CH_3$), or Pen(succinimide-N—($CH_2$)$_s$—NH—C(O)—($CH_2$)$_t$—$CH_3$);

$A^{17}$ is Ile, Abu, Acc, Aib, Ala, Cha, Leu, Nle, Phe, Tle, or Val;

$A^{18}$ is His, Amp, Arg, 2-Pal, 3-Pal, 4-Pal, Phe, or Tyr;

$A^{19}$ is Gln, Aib, or Asn;

$A^{20}$ is Gln, Aib, or Asn;

$A^{21}$ is Asp, Aib, or Glu;

$A^{22}$ is Phe, Acc, Aib, Aic, Cha, 1Nal, 2Nal, 2-Pal, 3-Pal, 4-Pal, ($X^4$, $X^5$, $X^6$, $X^7$, $X^8$)Phe, or Trp;

$A^{23}$ is Val, Abu, Acc, Aib, Ala, Cha, Ile, Leu, Nle, or Tle;

$A^{24}$ is Asn, Aib, or Gln;

$A^{25}$ is Trp, Acc, Aib, 1Nal, 2Nal, 2-Pal, 3-Pal, 4-Pal, Phe, or ($X^4$, $X^5$, $X^6$, $X^7$, $X^8$)Phe;

$A^{26}$ is Leu, Acc, Aib, Cha, Ile, Nle, Phe, ($X^4$, $X^5$, $X^6$, $X^7$, $X^8$)Phe, or Tle;

$A^{27}$ is Leu, Acc, Aib, Cha, Ile, Nle, Phe, ($X^4$, $X^5$, $X^6$, $X^7$, $X^8$)Phe, or Tle;

$A^{28}$ is Ala, Acc, or Aib;

$A^{29}$ is Gln, Aib, Asn, or deleted;

$A^{30}$ is Lys, Amp, Apc, Arg, hArg, Orn, HN—CH(($CH_2$)$_n$—N($R^4R^5$))—C(O), Cys(succinimide-N-alkyl), hCys(succinimide-N-alkyl), Pen(succinimide-N-alkyl), Cys(succinimide-N—($CH_2$)$_x$—C(O)—NH—($CH_2$)$_y$—$CH_3$), hCys(succinimide-N—($CH_2$)$_x$—C(O)—NH—($CH_2$)$_y$—$CH_3$), Pen(succinimide-N—($CH_2$)$_x$—C(O)—NH—($CH_2$)$_y$—$CH_3$), Cys(succinimide-N—($CH_2$)$_s$—NH—C(O)—($CH_2$)$_t$—$CH_3$), hCys(succinimide-N—($CH_2$)$_s$—NH—C(O)—($CH_2$)$_t$—$CH_3$), Pen(succinimide-N—($CH_2$)$_s$—NH—C(O)—($CH_2$)$_t$—$CH_3$), or deleted;

$A^{31}$ is Gly, Aib, Acc, β-Ala, HN—CH(($CH_2$)$_n$—N($R^4R^5$))—C(O), Cys(succinimide-N-alkyl), hCys(succinimide-N-alkyl), Pen(succinimide-N-alkyl), Cys(succinimide-N—($CH_2$)$_x$—C(O)—NH—($CH_2$)$_y$—$CH_3$), hCys(succinimide-N—($CH_2$)$_x$—C(O)—NH—($CH_2$)$_y$—$CH_3$), Pen(succinimide-N—($CH_2$)$_x$—C(O)—NH—($CH_2$)$_y$—$CH_3$), Cys(succinimide-N—($CH_2$)$_s$—NH—C(O)—($CH_2$)$_t$—$CH_3$), hCys(succinimide-N—($CH_2$)$_s$—NH—C(O)—($CH_2$)$_t$—$CH_3$), Pen(succinimide-N—($CH_2$)$_s$—NH—C(O)—($CH_2$)$_t$—$CH_3$), or deleted;

$A^{32}$ is Lys, Amp, Apc, Arg, hArg, Orn, HN—CH(($CH_2$)$_n$—N($R^4R^5$))—C(O), Cys(succinimide-N-alkyl), hCys(succinimide-N-alkyl), Pen(succinimide-N-alkyl), Cys(succinimide-N—($CH_2$)$_x$—C(O)—NH—($CH_2$)$_y$—$CH_3$), hCys(succinimide-N—($CH_2$)$_x$—C(O)—NH—($CH_2$)$_y$—$CH_3$), Pen(succinimide-N—($CH_2$)$_x$—C(O)—NH—($CH_2$)$_y$—$CH_3$), Cys(succinimide-N—($CH_2$)$_s$—NH—C(O)—($CH_2$)$_t$—$CH_3$), hCys(succinimide-N—($CH_2$)$_s$—NH—C(O)—($CH_2$)$_t$—$CH_3$), Pen(succinimide-N—($CH_2$)$_s$—NH—C(O)—($CH_2$)$_t$—$CH_3$), or deleted;

$A^{33}$ is Lys, Amp, Apc, Arg, hArg, Orn, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

$A^{34}$ is Asn, Aib, Gln, Ser, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

$A^{35}$ is Asp, Aib, Glu, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

$A^{36}$ is Trp, Acc, Aib, 1Nal, 2Nal, 2-Pal, 3-Pal, 4-Pal, Phe, (X$^4$, X$^5$, X$^6$, X$^7$, X$^8$)Phe, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

$A^{37}$ is Lys, Amp, Apc, Arg, hArg, Orn, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

$A^{38}$ is His, Amp, 2-Pal, 3-Pal, 4-Pal, Phe, Tyr, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

$A^{39}$ is Asn, Aib, Gln, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

$A^{40}$ is Ile, Acc, Aib, Ser, Thr, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

$A^{41}$ is Thr, Acc, Aib, Asn, Gln, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

$A^{42}$ is Gln, Acc, Aib, Asn, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

$A^{43}$ is Acc, Ado, Aib, Ala, Asn, Asp, His, Gln, Phe, Thr, Trp, Orn(N—C(O)—(CH$_2$)$_{10}$—CH$_3$), HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

$R^1$ is OH, NH$_2$, (C$_1$-C$_{30}$)alkoxy, or NH—X$^2$—CH$_2$—Z$^0$, wherein X$^2$ is a (C$_0$-C$_{30}$) hydrocarbon moiety and Z$^0$ is H, OH, CO$_2$H, or CONH$_2$;

each of R$^2$, R$^3$, R$^4$ and R$^5$ is independently selected from the group consisting of H, (C$_1$-C$_{30}$)alkyl, (C$_1$-C$_{30}$)heteroalkyl, (C$_1$-C$_{30}$)acyl, (C$_2$-C$_{30}$)alkenyl, (C$_2$-C$_{30}$)alkynyl, aryl(C$_1$-C$_{30}$)alkyl, aryl(C$_1$-C$_{30}$)acyl, substituted (C$_1$-C$_{30}$)alkyl, substituted (C$_1$-C$_{30}$)heteroalkyl, substituted (C$_1$-C$_{30}$)acyl, substituted (C$_2$-C$_{30}$)alkenyl, substituted (C$_2$-C$_{30}$)alkynyl, substituted aryl(C$_1$-C$_{30}$)alkyl, and substituted aryl(C$_1$-C$_{30}$)acyl; provided that when R$^2$ is (C$_1$-C$_{30}$)acyl, aryl(C$_1$-C$_{30}$)acyl, substituted (C$_1$-C$_{30}$)acyl, or substituted aryl(C$_1$-C$_{30}$)acyl, then R$^3$ is H, (C$_1$-C$_{30}$)alkyl, (C$_1$-C$_{30}$)heteroalkyl, (C$_2$-C$_{30}$)alkenyl, (C$_2$-C$_{30}$)alkynyl, aryl(C$_1$-C$_{30}$)alkyl, substituted (C$_1$-C$_{30}$)alkyl, substituted (C$_1$-C$_{30}$)heteroalkyl, substituted (C$_2$-C$_{30}$)alkenyl, substituted (C$_2$-C$_{30}$)alkynyl, or substituted aryl(C$_1$-C$_{30}$)alkyl; further provided that when R$^4$ is (C$_1$-

$C_{30}$)acyl, aryl($C_1$-$C_{30}$)acyl, substituted ($C_1$-$C_{30}$)acyl, or substituted aryl($C_1$-$C_{30}$)acyl, then $R^5$ is H, ($C_1$-$C_{30}$)alkyl, ($C_1$-$C_{30}$)heteroalkyl, ($C_2$-$C_{30}$)alkenyl, ($C_2$-$C_{30}$)alkynyl, aryl($C_1$-$C_{30}$)alkyl, substituted ($C_1$-$C_{30}$)alkyl, substituted ($C_1$-$C_{30}$)heteroalkyl, substituted ($C_2$-$C_{30}$)alkenyl, substituted ($C_2$-$C_{30}$)alkynyl, or substituted aryl ($C_1$-$C_{30}$)alkyl;

n is, independently for each occurrence, an integer from 1 to 5 inclusive;

s, t, x and y each is, independently for each occurrence, an integer from 1 to 30 inclusive;

$X^4$, $X^5$, $X^6$, $X^7$ and $X^8$ each is, independently for each occurrence, H, F, $CF_3$, Cl, Br, I, ($C_{1-10}$)alkyl, substituted ($C_{1-10}$)alkyl, aryl, substituted aryl, OH, $NH_2$, —$CH_2NH_2$, $NO_2$, or CN;

wherein the bond between $A^1$ and $A^2$ is a peptide or pseudopeptide bond; and wherein the compound optionally further comprises a covalently linked PEG moiety;

provided that when $A^1$ is 4Hppa, then $R^2$ and $R^3$ are deleted;

further provided that at least one amino acid residue at positions 2 and 3 is not the amino acid residue of the corresponding position in native hGIP; and further provided that at least one amino acid residue at positions 7, 11, 13, 14, 40, 41, and 43 is not the amino acid residue of the corresponding position in native hGIP;

or a pharmaceutically acceptable salt thereof.

2. The compound according to claim 1, wherein:

$A^1$ is Cpa, His, 4Hppa, 2Pal, 3Pal, 4Pal, 3Br-Phe, 4$CF_3$-Phe, 3Cl-Phe, 4CN-Phe, 3F-Phe, 4F-Phe, 3,4F-Phe, 3,5F-Phe, 3,4,5F-Phe, 4Me-Phe, 4$NH_2$-Phe, 4$NH_2CH_2$-Phe, 3OH-Phe, Taz, 3Thi, 7HO-Tic, Tyr(Ac), Tyr(Me), β-Tyr, 3Br-Tyr, 3,5Br-Tyr, 3Cl-Tyr, 2F-Tyr, 3F-Tyr, hTyr, 3I-Tyr, 3,5I-Tyr, αMe-Tyr, 2,6Me-Tyr, 3MeO-Tyr, 3$NH_2$-Tyr, 3$NO_2$-Tyr, 3OH-Tyr, or 3(HO—$CH_2$)Tyr;

$A^2$ is Ala, Aib, Gly;
$A^3$ is Glu, 4Hyp, or hPro;
$A^4$ is Gly;
$A^5$ is Thr;
$A^6$ is Phe;
$A^7$ is Ile, A5c, or A6c;
$A^8$ is Ser;
$A^9$ is Asp;
$A^{10}$ is Tyr;
$A^{11}$ is Ser, A5c, or Aib;
$A^{12}$ is Ile;
$A^{13}$ is Ala or Aib;
$A^{14}$ is Met, A5c, or Nle;
$A^{15}$ is Asp;
$A^{16}$ is Lys;
$A^{17}$ is Ile;
$A^{18}$ is His;
$A^{19}$ is Gln;
$A^{20}$ is Gln;
$A^{21}$ is Asp;
$A^{22}$ is Phe;
$A^{23}$ is Val;
$A^{24}$ is Asn;
$A^{25}$ is Trp;
$A^{26}$ is Leu;
$A^{27}$ is Leu;
$A^{28}$ is Ala;
$A^{29}$ is Gln;
$A^{30}$ is Lys;
$A^{31}$ is Gly or deleted;
$A^{32}$ is Lys or deleted;
$A^{33}$ is Lys or deleted;
$A^{34}$ is Asn or deleted;
$A^{35}$ is Asp or deleted;
$A^{36}$ is Trp or deleted;
$A^{37}$ is Lys or deleted;
$A^{38}$ is His or deleted;
$A^{39}$ is Asn or deleted;
$A^{40}$ is Ile, A5c, or deleted;
$A^{41}$ is Thr, A5c, or deleted;
$A^{42}$ is Gln or deleted; and
$A^{43}$ is His, Cys(succinimide-N—$(CH_2)_{11}$—$CH_3$), Orn (N—C(O)—$(CH_2)_{10}$—$CH_3$), or deleted;
or a pharmaceutically acceptable salt thereof.

3. The compound according to claim 2, wherein said compound is:

(4Hppa$^1$, Aib$^2$, A5c$^7$, Nle$^{14}$)hGIP(1-30)-$NH_2$ (SEQ ID NO:4);
(4Hppa$^1$, Aib$^{2,11}$, Nle$^{14}$)hGIP(1-30)-$NH_2$ (SEQ ID NO:5);
(4Hppa$^1$, Aib$^2$, A5c$^7$)hGIP(1-30)-$NH_2$ (SEQ ID NO:6);
(4Hppa$^1$, Aib$^{2,11}$)hGIP(1-30)-$NH_2$ (SEQ ID NO:7);
(4Hppa$^1$, Aib$^2$, Nle$^{14}$)hGIP(1-30)-$NH_2$ (SEQ ID NO:8);
(4Hppa$^1$, 4Hyp$^3$, A6c$^7$)hGIP(1-42)-OH (SEQ ID NO:10);
(4Hppa$^1$, hPro$^3$, A6c$^7$)hGIP(1-42)-OH (SEQ ID NO:11);
(4Hppa$^1$, Aib$^2$, hPro$^3$, Nle$^{14}$)hGIP(1-30)-$NH_2$ (SEQ ID NO:12);
(His$^1$, Aib$^{2,13}$, Nle$^{14}$)hGIP(1-42)-OH (SEQ ID NO:13);
(3,5Br-Tyre, Aib$^{2,13}$, Nle$^{14}$)hGIP(1-42)-OH (SEQ ID NO:14);
(His$^1$, Aib$^2$, A5c$^{11}$, Nle$^{14}$)hGIP(1-42)-OH (SEQ ID NO:15);
(3,5Br-Tyr$^1$, Aib$^2$, A5c$^{11}$, Nle$^{14}$)hGIP(1-42)-OH (SEQ ID NO:16);
(3Cl-Tyr$^1$, Aib$^2$, A5c$^{11}$, Nle$^{14}$)hGIP(1-42)-OH (SEQ ID NO:17);
(3Br-Tyr$^1$, Aib$^2$, A5c$^{11}$, Nle$^{14}$)hGIP(1-42)-OH (SEQ ID NO:18);
(3I-Tyr$^1$, Aib$^2$, A5c$^{11}$, Nle$^{14}$)hGIP(1-42)-OH (SEQ ID NO:19);
(3,5I-Tyr$^1$, Aib$^2$, A5c$^{11}$, Nle$^{14}$)hGIP(1-42)-OH (SEQ ID NO:20);
(4$NH_2$-Phe$^1$, Aib$^2$, A5c$^{11}$, Nle$^{14}$)hGIP(1-42)-OH (SEQ ID NO:21);
(hTyr$^1$, Aib$^2$, A5c$^{11}$, Nle$^{14}$)hGIP(1-42)-OH (SEQ ID NO:22);
(Cpa$^1$, Aib$^2$, A5c$^{11}$, Nle$^{14}$)hGIP(1-42)-OH (SEQ ID NO:23);
(4$NH_2CH_2$-Phe$^1$, Aib$^2$, A5c$^{11}$, Nle$^{14}$)hGIP(1-42)-OH (SEQ ID NO:24);
(3,4,5F-Phe$^1$, Aib$^2$, A5c$^{11}$, Nle$^{14}$)hGIP(1-42)-OH (SEQ ID NO:25);
(3F-Phe$^1$, Aib$^2$, A5c$^{11}$, Nle$^{14}$)hGIP(1-42)-OH (SEQ ID NO:26);
(3,4F-Phe$^1$, Aib$^2$, A5c$^{11}$, Nle$^{14}$)hGIP(1-42)-OH (SEQ ID NO:27);
(3,5F-Phe$^1$, Aib$^2$, A5c$^{11}$, Nle$^{14}$)hGIP(1-42)-OH (SEQ ID NO:28);
(3OH-Phe$^1$, Aib$^2$, A5c$^{11,41}$)hGIP(1-42)-OH (SEQ ID NO:29);
(3OH-Tyr$^1$, Aib$^2$, A5c$^{11,41}$)hGIP(1-42)-OH (SEQ ID NO:30);
(3MeO-Tyr$^1$, Aib$^2$, A5c$^{11,41}$)hGIP(1-42)-OH (SEQ ID NO:31);
[Tyr(Ac)$^1$, Aib$^2$, A5c$^{11,41}$]hGIP(1-42)-OH (SEQ ID NO:32);
(2,6Me-Tyr$^1$, Aib$^2$, A5c$^{11,41}$)hGIP(1-42)-OH (SEQ ID NO:33);

[Tyr(Me)$^1$, Aib$^2$, A5c$^{11,41}$]hGIP(1-42)-OH (SEQ ID NO:34);
(4F-Phe$^1$, Aib$^2$, A5c$^{11,41}$)hGIP(1-42)-OH (SEQ ID NO:35);
(4-Pal$^1$, Aib$^2$, A5c$^{11,41}$)hGIP(1-42)-OH (SEQ ID NO:36);
(3-Pal$^1$, Aib$^2$, A5c$^{11,41}$)hGIP(1-42)-OH (SEQ ID NO:37);
(Taz$^1$, Aib$^2$, A5c$^{11,41}$)hGIP(1-42)-OH (SEQ ID NO:38);
(3NO$_2$-Tyr$^1$, Aib$^2$, A5c$^{11,41}$)hGIP(1-42)-OH (SEQ ID NO:39);
(3Thi$^1$, Aib$^2$, A5c$^{11,41}$)hGIP(1-42)-OH (SEQ ID NO:40);
(4CN-Phe$^1$, Aib$^2$, A5c$^{11,41}$)hGIP(1-42)-OH (SEQ ID NO:41);
(3F-Tyr$^1$, Gly$^2$, A5c$^{11,40}$)hGIP(1-42)-OH (SEQ ID NO:42);
(3F-Phe$^1$, Aib$^2$, A5c$^{11,41}$)hGIP(1-42)-OH (SEQ ID NO:44);
(3Cl-Phe$^1$, Aib$^2$, A5c$^{11,41}$)hGIP(1-42)-OH (SEQ ID NO:45);
(3Br—Phe$^1$, Aib$^2$, A5c$^{11,41}$)hGIP(1-42)-OH (SEQ ID NO:46);
(3Cl-Tyr$^1$, Aib$^2$, A5c$^{11,41}$)hGIP(1-42)-OH (SEQ ID NO:47);
(3Br-Tyr$^1$, Aib$^2$, A5c$^{11,41}$)hGIP(1-42)-OH (SEQ ID NO:48);
(β-Tyr$^1$, Aib$^2$, A5c$^{11,41}$)hGIP(1-42)-OH (SEQ ID NO:49);
(3F-Tyr$^1$, Aib$^2$, A5c$^{11,41}$)hGIP(1-42)-OH (SEQ ID NO:50);
(2F-Tyr$^1$, Aib$^2$, A5c$^{11,41}$)hGIP(1-42)-OH (SEQ ID NO:51);
(αMe-Tyr$^1$, Aib$^2$, A5c$^{11,41}$)hGIP(1-42)-OH (SEQ ID NO:52);
(3NH$_2$-Tyr$^1$, Aib$^2$, A5c$^{11,41}$)hGIP(1-42)-OH (SEQ ID NO:53);
(2-Pal$^1$, Aib$^2$, A5c$^{11,41}$)hGIP(1-42)-OH (SEQ ID NO:54);
[3(HO—CH$_2$)Tyr$^1$, Aib$^2$, A5c$^{11,41}$]hGIP(1-42)-OH (SEQ ID NO:55);
(2,6Me-Tyr$^1$, Aib$^2$, A5c$^{11}$, His$^{43}$)hGIP(1-43)-OH (SEQ ID NO:56);
(2,6Me-Tyr$^1$, Aib$^2$, A5c$^{11,14}$, His$^{43}$)hGIP(1-43)-OH (SEQ ID NO:57);
(2,6Me-Tyr$^1$, Aib$^2$, A5c$^{11,14}$, Nle$^{14}$, His$^{43}$)hGIP(1-43)-OH (SEQ ID NO:58);
(3F-Phe$^1$, Aib$^2$, A5c$^{11,14, 41}$)hGIP(1-42)-OH (SEQ ID NO:59);
(3F-Phe$^1$, Aib$^2$, A5c$^{11, 41}$, Nle$^{14}$, His$^{43}$)hGIP(1-43)-OH (SEQ ID NO:60);
(3F-Phe$^1$, Aib$^2$, A5c$^{11, 41}$, His$^{43}$)hGIP(1-43)-OH (SEQ ID NO:61);
(3F-Phe$^1$, Aib$^2$, A5c$^{14, 41}$, His$^{43}$)hGIP(1-43)-OH (SEQ ID NO:62);
(3Cl-Tyr$^1$, D-Aib$^2$, A5c$^{11}$, Nle$^{14}$, His$^{43}$)hGIP(1-43)-OH;
(3Cl-Tyr$^1$, D-Ala$^2$, A5c$^{11,14}$, His$^{43}$)hGIP(1-43)-OH;
(3Cl-Tyr$^1$, Aib$^2$, A5c$^{11,14}$, His$^{43}$)hGIP(1-43)-OH (SEQ ID NO:63);
(3Cl-Tyr$^1$, Aib$^2$, A5c$^{11}$, Nle$^{14}$, His$^{43}$)hGIP(1-43)-OH (SEQ ID NO:64);
[3Cl-Tyr$^1$, Aib$^2$, A5c$^{11}$, Nle$^{14}$, Orn$^{43}$(N—C(O)—(CH$_2$)$_{10}$—CH$_3$)]hGIP(1-43)-OH (SEQ ID NO:65);
[3Cl-Tyr$^1$, Aib$^2$, A5c$^{11}$, Nle$^{14}$, Cys$^{43}$(succinimide-N—(CH$_2$)$_{11}$—CH$_3$)]hGIP(1-43)-OH (SEQ ID NO:66);
[3Cl-Tyr$^1$, D-Ala$^2$, A5c$^{11}$, Nle$^{14}$, Orn$^{43}$(N—C(O)—(CH$_2$)$_{10}$—CH$_3$)]hGIP(1-43)-OH;
[3Cl-Tyr$^1$, D-Alae, A5c$^{11}$, Nle$^{14}$, Cys$^{43}$(succinimide-N—(CH$_2$)$_{11}$—CH$_3$)]hGIP(1-43)-OH;
[3Cl-Tyr$^1$, D-Ala-2, A5c$^{11, 14}$, Orn$^{43}$(N—C(O)—(CH$_2$)$_{10}$—CH$_3$)]hGIP(1-43)-OH;
[3Cl-Tyr$^1$, D-Ala$^2$, A5c$^{11,14}$, Cys$^{43}$(succinimide-N—(CH$_2$)$_{11}$—CH$_3$)]hGIP(1-43)-OH;
(3Br-Tyr$^1$, Aib$^2$, A5c$^{11}$, Nle$^{14}$, His$^{43}$)hGIP(1-43)-OH (SEQ ID NO:67);
(3Br-Tyr$^1$, Aib$^2$, A5c$^{11, 14}$, His$^{43}$)hGIP(1-43)-OH (SEQ ID NO:68);
(3MeO-Tyr$^1$, Aib$^2$, A5c$^{11}$, His$^{43}$)hGIP(1-43)-OH (SEQ ID NO:69);
(3MeO-Tyr$^1$, Aib$^2$, A5c$^{11,14}$, His$^{43}$)hGIP(1-43)-OH (SEQ ID NO:70);
(3MeO-Tyr$^1$, Aib$^2$, A5c$^{11,14, 41}$, His$^{43}$)hGIP(1-43)-OH (SEQ ID NO:71);
(4CN-Phe$^1$, Aib$^2$, A5c$^{11}$, His$^{43}$)hGIP(1-43)-OH (SEQ ID NO:72);
(7HO-Tic$^1$, Aib$^2$, A5c$^{11}$, His$^{43}$)hGIP(1-43)-OH (SEQ ID NO:73);
(4Me-Phe$^1$, Aib$^2$, A5c$^{11}$, His$^{43}$)hGIP(1-43)-OH (SEQ ID NO:74);
(4CN-Phe$^1$, Aib$^2$, A5c$^{11}$, His$^{43}$)hGIP(1-43)-OH (SEQ ID NO:75);
(hTyr$^1$, Aib$^2$, A5c$^{11}$, His$^{43}$)hGIP(1-43)-OH (SEQ ID NO:76);
[3Cl-Tyr$^1$, D-Ala$^2$, A5c$^{11}$, Nle$^{14}$, Lys$^{43}$(N—C(O)—(CH$_2$)$_{10}$—CH$_3$)]hGIP(1-43)-OH;
[3Cl-Tyr$^1$, D-Ala$^2$, A5c$^{11,14}$, Lys$^{43}$(N—C(O)—(CH$_2$)$_{10}$—CH$_3$)]hGIP(1-43)-OH;
[3Cl-Tyr$^1$, Aib$^2$, A5c$^{11}$, Nle$^{14}$, Lys$^{43}$(N—C(O)—(CH$_2$)$_{10}$—CH$_3$)]hGIP(1-43)-OH (SEQ ID NO:77);
[3Cl-Tyr$^1$, Aib$^2$, A5c$^{11, 14}$, Lys$^{43}$(N—(O)—(CH$_2$)$_{10}$—CH$_3$)]hGIP(1-43)-OH (SEQ ID NO:78);
(3Cl-Tyr$^1$, Aib$^2$, A5c$^{11}$, Nle$^{14}$, Cys$^{43}$)hGIP(1-43)-OH (SEQ ID NO:79);
[3Cl-Tyr$^1$, D-Alae, A5c$^{11}$, Nle$^{14}$, Cys$^{43}$(succinimide)]hGIP(1-43)-OH; or
[3Cl-Tyr$^1$, D-Alae, A5c$^{11,14}$, Cys$^{43}$(succinimide)]hGIP(1-43)-OH;
or a pharmaceutically acceptable salt thereof.

4. The compound according to claim 2, wherein: A$^1$ is 4Hppa; A$^{43}$ is deleted; at least one of A$^2$, and is not the amino acid residue of the corresponding position in native hGIP; and at least one of A$^7$, A$^{11}$, and A$^{14}$ is not the amino acid residue of the corresponding position in native hGIP; or a pharmaceutically acceptable salt thereof.

5. The compound according to claim 1, wherein: A1 is Tyr(Ac), Tyr(Me), β-Tyr, 3Br-Tyr, 3,5Br-Tyr, 3Cl-Tyr, 2F-Tyr, 3F-Tyr, hTyr, 3I-Tyr, 3,5I-Tyr, αMe-Tyr, 2,6Me-Tyr, 3MeO-Tyr, 3NH$_2$-Tyr, 3NO$_2$-Tyr, 3OH-Tyr, or 3(HO—CH$_2$)Tyr; A$^2$ is A5c, A6c, Aib, D-Ala, Gly, or Ser; and at least one of A$^{11}$, A$^{13}$, A$^{14}$, A$^{40}$, A$^{41}$ and A$^{43}$ is not the amino acid residue of the corresponding position in native hGIP; or a pharmaceutically acceptable salt thereof.

6. The compound according to claim 5, wherein: A$^2$ is Aib, D-Ala, or Gly; and at least two of A$^{11}$, A$^{13}$, A$^{14}$, A$^{40}$, A$^{41}$ and A$^{43}$ are not the amino acid residues of the corresponding positions in native hGIP; or a pharmaceutically acceptable salt thereof.

7. The compound according to claim 1, wherein: A$^1$ is 3Br-Phe, 3Cl-Phe, 4CN-Phe, 3F-Phe, 4F-Phe, 3,4F-Phe, 3,4,5F-Phe, 3,5F-Phe, 4NH$_2$-Phe, 4NH$_2$CH$_2$-Phe, or 3OH-Phe; A$^2$ is A5c, A6c, Aib, D-Ala, Gly, or Ser; A$^{11}$ is A5c; and at least one of A$^{14}$ and A$^{41}$ is not the amino acid residue of the corresponding position in native hGIP; or a pharmaceutically acceptable salt thereof.

8. The compound according to claim 7, wherein: A$^2$ is Aib; or a pharmaceutically acceptable salt thereof.

9. The compound according to claim 1, wherein said compound is:
(3Cl-Tyr$^1$, Aib$^2$, A5c$^{11}$, Nle$^{14}$)hGIP(1-42)-OH (SEQ ID NO:17);
(3Cl-Tyr$^1$, Aib$^2$, A5c$^{11}$, Nle$^{14}$, Cys$^{43}$)hGIP(1-43)-OH (SEQ ID NO:79);
[3Cl-Tyr$^1$, Aib$^2$, A5c$^{11}$, Nle$^{14}$, Cys$^{43}$(succinimide-N-20K PEG)]hGIP(1-43)-NH$_2$ (SEQ ID NO:80);
[3Cl-Tyr$^1$, D-Ala$^2$, A5c$^{11}$, Nle$^{14}$, Lys$^{43}$(N—C(O)—(CH$_2$)$_{10}$—CH$_3$)]hGIP(1-43)-OH;
[3Cl-Tyr$^1$, Aib$^2$, A5c$^{11}$, Nle$^{14}$, Cys$^{43}$(succinimide-N-30K PEG)]hGIP(1-43)-NH$_2$ (SEQ ID NO:81);
[3Cl-Tyr$^1$, Aib$^2$, A5c$^{11}$, Nle$^{14}$, Cys$^{43}$(succinimide-N—(CH$_2$)$_2$—C(O)NH—(CH$_2$)$_3$—O—CH$_2$—CH(20K PEG)-CH$_2$-20K PEG)]hGIP(1-43)-NH$_2$ (SEQ ID NO:87);
(3Br-Tyr$^1$, Aib$^2$, A5c$^{11,14}$, His$^{43}$)hGIP(1-43)-OH (SEQ ID NO:68);
(3Br-Tyr$^1$, Aib$^2$, A5c$^{11}$, Nle$^{14}$)hGIP(1-42)-OH (SEQ ID NO:18);
[Tyr(Me)$^1$, Aib$^2$, A5c$^{11}$,]hGIP(1-42)-OH (SEQ ID NO:32);
(3Cl-Tyr$^1$, Aib$^2$, A5c$^{11}$, Nle$^{14}$, His$^{43}$)hGIP(1-43)-OH (SEQ ID NO:64);
(3Cl-Tyr$^1$, Aib$^2$, A5c$^{11,14}$, His$^{43}$)hGIP(1-43)-OH (SEQ ID NO:63);
(3MeO-Tyr$^1$, Aib$^2$, A5c$^{11,41}$)hGIP(1-42)-OH (SEQ ID NO:31);
[3Cl-Tyr$^1$, D-Ala$^2$, A5c$^{11,14}$, Cys$^{43}$(succinimide)]hGIP(1-43)-OH;
(3F-Phe$^1$, Aib$^2$, A5c$^{11}$, Nle$^{14}$)hGIP(1-42)-OH (SEQ ID NO:26);
(4Hppa$^1$, Aib$^2$, Nle$^{14}$)hGIP(1-30)-NH$_2$ (SEQ ID NO:8);
(His$^1$, Aib$^2$, A5c$^{11}$, Nle$^{14}$)hGIP(1-42)-OH (SEQ ID NO:15);
(3OH-Phe$^1$, Aib$^2$, A5c$^{11, 41}$)hGIP(1-42)-OH (SEQ ID NO:29);
[Tyr(Me)$^1$, Aib$^2$, A5c$^{11, 41}$]hGIP(1-42)-OH (SEQ ID NO:34);
(3Thi$^1$, Aib$^2$, A5c$^{11,41}$)hGIP(1-42)-OH (SEQ ID NO:40);
or a pharmaceutically acceptable salt thereof.

10. The compound according to claim 1, wherein said compound is:
(3Cl-Tyr$^1$, Aib$^2$, A5c$^{11}$, Nle$^{14}$)hGIP(1-42)-OH (SEQ ID NO:17);
(3Cl-Tyr$^1$, Aib$^2$, A5c$^{11}$, Nle$^{14}$, Cys$^{43}$)hGIP(1-43)-OH (SEQ ID NO:79);
[3Cl-Tyr$^1$, Aib$^2$, A5c$^{11}$, Nle$^{14}$, Cys$^{43}$(succinimide-N-20K PEG)]hGIP(1-43)-NH$_2$ (SEQ ID NO:80);
[3Cl-Tyr$^1$, D-Ala$^2$, A5c$^{11}$, Nle$^{14}$, Lys$^{43}$(N—C(O)—(CH$_2$)$_{10}$—CH$_3$)]hGIP(1-43)-OH;
[3Cl-Tyr$^1$, Aib$^2$, A5c$^{11}$, Nle$^{14}$, Cys$^{43}$(succinimide-N-30K PEG)]hGIP(1-43)-NH$_2$ (SEQ ID NO:81); and
[3Cl-Tyr$^1$, Aib$^2$, A5c$^{11}$, Nle$^{14}$, Cys$^{43}$(succinimide-N—(CH$_2$)$_2$—C(O)NH—(CH$_2$)$_3$—O—CH$_2$—CH(20K PEG)-CH$_2$-20K PEG)]hGIP(1-43)-NH$_2$ (SEQ ID NO:87);
or a pharmaceutically acceptable salt thereof.

11. The compound according to claim 1, wherein said compound is (3Cl-Tyr$^1$, Aib$^2$, A5c$^{11}$, Nle$^{14}$)hGIP(1-42)-OH (SEQ ID NO:17) or a pharmaceutically acceptable salt thereof.

12. The compound according to claim 1, wherein the peptide bond between A$^1$ and A$^2$ is a pseudopeptide bond$_7$; or a pharmaceutically acceptable salt thereof.

13. The compound according to claim 1, further comprising a covalently linked PEG moiety,
wherein said PEG moiety is covalently linked to the compound via a Cys(maleimide), hCys(maleimide), or Pen (maleimide) linker, to form Cys(succinimide-N-PEG), hCys(succinimide-N-PEG), or Pen(succinimide-N-PEG), and
wherein said PEG is selected from the group consisting of 5K PEG, 10K PEG, 20K PEG, 30K PEG, 40K PEG, 50K PEG, and 60K PEG, to form Cys(succinimide-N-5K PEG), Cys(succinimide-N-10K PEG), Cys(succinimide-N-20K PEG), Cys(succinimide-N-30K PEG), Cys(succinimide-N-40K PEG), Cys(succinimide-N-50K PEG), Cys(succinimide-N-60K PEG), hCys(succinimide-N-5K PEG), hCys(succinimide-N-10K PEG), hCys(succinimide-N-20K PEG), hCys(succinimide-N-30K PEG), hCys(succinimide-N-40K PEG), hCys(succinimide-N-50K PEG), hCys(succinimide-N-60K PEG), Pen(succinimide-N-5K PEG), Pen(succinimide-N-10K PEG), Pen(succinimide-N-20K PEG), Pen(succinimide-N-30K PEG), Pen(succinimide-N-40K PEG), Pen(succinimide-N-50K PEG), or Pen(succinimide-N-60K PEG);
or a pharmaceutically acceptable salt thereof.

14. A pharmaceutical composition comprising an effective amount of a compound of claim 1.

15. A method for treating conditions or diseases mediated by GIP-receptor binding, comprising the step of administering to a subject in need thereof a therapeutically effective amount of a compound claim 1, wherein said condition or disease is selected from the group consisting of type 1 diabetes, type 2 diabetes, obesity, insulin resistance, glucose intolerance, fatty liver, glucagonomas, secretory disorders of the airway, metabolic disorders, arthritis, osteoporosis, central nervous system disease, restenosis, neurodegenerative disease, renal failure, congestive heart failure, nephrotic syndrome, cirrhosis, pulmonary edema, hypertension, and disorders wherein the reduction of food intake and/or losing body weight is desired.

16. The method of claim 15, wherein said condition or disease is type 2 diabetes.

17. A method of treating a diabetes-related disorder, comprising the step of administering to a subject in need thereof a therapeutically effective amount of a compound of claim 1, wherein said diabetes-related disorder is selected from the group consisting of hyperglycemia, hyperinsulinemia, impaired glucose tolerance, impaired fasting glucose, dyslipidemia, hypertriglyceridemia, and insulin resistance.

18. A method of stimulating insulin secretion in a subject in need thereof by administering to said subject a therapeutically effective amount of compound of claim 1.

* * * * *

UNITED STATES PATENT AND TRADEMARK OFFICE
CERTIFICATE OF CORRECTION

PATENT NO.        : 8,999,940 B2
APPLICATION NO.   : 13/057966
DATED             : April 7, 2015
INVENTOR(S)       : Zheng Xin Dong et al.

It is certified that error appears in the above-identified patent and that said Letters Patent is hereby corrected as shown below:

In the claims:

Claim 1, Column 123, Line 21 that portion of the claims that reads "$A^{13}$-$A^{14}$-$A^{15}$-$A^{16}$-$A^{17}$-$A^{18}$-$A^{19}$-$A^{20}A^{21}$-$A^{22}$-" should read -- $A^{13}$-$A^{14}$-$A^{15}$-$A^{16}$-$A^{17}$-$A^{18}$-$A^{19}$-$A^{20}$-$A^{21}$-$A^{22}$- --

Claim 1, Column 123, Line 51 that portion of the claims that reads "$A^{13}$ is Ala, Acc, Aib, p-Ala, D-Ala, Gly, or Ser;" should read -- $A^{13}$ is Ala, Acc, Aib, β-Ala, D-Ala, Gly, or Ser; --

Claim 3, Column 128, Line 28 that portion of the claims that reads "(3,5Br-Tyre, $Aib^{2,\,13}$, $Nle^{14}$)hGIP(1-42)-OH (SEQ ID NO:14);" should read -- (3,5Br-$Tyr^1$, $Aib^{2,\,13}$, $Nle^{14}$)hGIP(1-42)-OH (SEQ ID NO:14); --

Claim 3, Column 128, Line 38 that portion of the claims that reads "(31-$Tyr^1$, $Aib^2$, $A5c^{11}$, $Nle^{14}$)hGIP(1-42)-OH (SEQ ID NO:19);" should read -- (3I-$Tyr^1$, $Aib^2$, $A5c^{11}$, $Nle^{14}$)hGIP(1-42)-OH (SEQ ID NO:19); --

Claim 3, Column 128, Line 40 that portion of the claims that reads "(3,51-$Tyr^1$, $Aib^2$, $A5c^{11}$, $Nle^{14}$)hGIP(1-42)-OH (SEQ ID NO:20);" should read -- (3,5I-$Tyr^1$, $Aib^2$, $A5c^{11}$, $Nle^{14}$)hGIP(1-42)-OH (SEQ ID NO:20); --

Claim 3, Column 129, Line 42 that portion of the claims that reads "(2,6Me-$Tyr^1$, $Aib^2$, $A5c^{11,14}$, $Nle^{14}$, $His^{43}$)hGIP(1-43)-OH)" should read -- (2,6Me-$Tyr^1$, $Aib^2$, $A5c^{11}$, $Nle^{14}$, $His^{43}$)hGIP(1-43)-OH --

Signed and Sealed this
Twenty-first Day of June, 2016

Michelle K. Lee
*Director of the United States Patent and Trademark Office*

CERTIFICATE OF CORRECTION (continued)
U.S. Pat. No. 8,999,940 B2

In the claims:

Claim 3, Column 129, Line 50 that portion of the claims that reads "(3F-Phe$^1$, Aib$^2$, A5c$^{14, 41}$, His$^{43}$)hGIP(1-43)-OH (SEQ ID NO:62);" should read -- (3F-Phe$^1$, Aib$^2$, A5c$^{11, 14, 41}$, His$^{43}$)hGIP(1-43)-OH (SEQ ID NO:62) --

Claim 3, Column 129, Line 52 that portion of the claims that reads "(3Cl-Tyr$^1$, D-Aib$^2$, A5c$^{11}$, Nle$^{14}$, His$^{43}$)hGIP(1-43)-OH;" should read -- (3Cl-Tyr$^1$, D-Ala$^2$, A5c$^{11}$, Nle$^{14}$, His$^{43}$)hGIP(1-43)-OH; --

Claim 3, Column 129, Line 64 that portion of the claims that reads "[3Cl-Tyr$^1$, D-Alae, A5c$^{11}$, Nle$^{14}$, Cys$^{43}$(succinimide-N-(CH$_2$)$_{11}$-CH$_3$)]hGIP(1-43)-OH;" should read -- [3Cl-Tyr$^1$, D-Ala$^2$, A5c$^{11}$, Nle$^{14}$, Cys$^{43}$(succinimide-N-(CH$_2$)]$_{11}$-CH$_3$)]hGIP(1-43)-OH; --

Claim 3, Column 129, Line 66 that portion of the claims that reads "[3Cl-Tyr$^1$, D-Alae, A5c$^{11}$, Nle$^{14}$, Cys$^{43}$(succinimide-N-(CH$_2$)$_{11}$-CH$_3$)]hGIP(1-43)-OH;" should read -- [3Cl-Tyr$^1$, D-Ala$^2$, A5c$^{11}$, Nle$^{14}$, Cys$^{43}$(succinimide-N-(CH$_2$)$_{11}$-CH$_3$)]hGIP(1-43)-OH; --

Claim 3, Column 130, Line 13 that portion of the claims that reads "[3Cl-Tyr$^1$, D-Ala-2, A5c$^{11, 14}$, Orn$^{43}$(N-C(O)-(CH$_2$)$_{10}$-CH$_3$)]hGIP(1-43)-OH;" should read -- [3Cl-Tyr$^1$, D-Ala$^2$, A5c$^{11, 14}$, Orn$^{43}$(N-C(O)-(CH$_2$)$_{10}$-CH$_3$)]hGIP(1-43)-OH; --

Claim 3, Column 130, Line 35 that portion of the claims that reads "[3Cl-Tyr$^1$, D-Alae, A5c$^{11}$, Nle$^{14}$, Cys$^{43}$(succinimide)]hGIP(1-43)-OH; or" should read -- [3Cl-Tyr$^1$, D-Ala$^2$, A5c$^{11}$, Nle$^{14}$, Cys$^{43}$(succinimide)]hGIP(1-43)-OH; or --

Claim 3, Column 130, Line 37 that portion of the claims that reads "[3Cl-Tyr$^1$, D-Alae, A5c$^{11, 14}$, Cys$^{43}$(succinimide)]hGIP(1-43)-OH;" should read -- [3Cl-Tyr$^1$, D-Ala$^2$, A5c$^{11, 14}$, Cys$^{43}$(succinimide)]hGIP(1-43)-OH; --

Claim 5, Column 130, Line 48 that portion of the claims that reads "2F-Tyr, 3F-Tyr, hTyr, 31-Tyr, 3,5I-Tyr, αMe-Tyr, 2,6Me-Tyr," should read -- 2F-Tyr, 3F-Tyr, hTyr, 3I-Tyr, 3,5I-Tyr, αMe-Tyr, 2,6Me-Tyr, --

Claim 9, Column 131, Line 21 that portion of the claims that reads "[Tyr(Me)$^1$, Aib$^2$, A5c$^{11}$]hGIP(1-42)-OH (SEQ ID NO:32);" should read -- [Tyr(Ac)$^1$, Aib$^2$, A5c$^{11, 41}$]hGIP(1-42)-OH (SEQ ID NO:32); --

CERTIFICATE OF CORRECTION (continued)
U.S. Pat. No. 8,999,940 B2

In the claims:

Claim 12, Column 132, Lines 5-7 the claim that reads "The_compound according to claim 1, wherein the peptide bond between $A^1$ and $A^2$ is a pseudopeptide bond$_7$; or a pharmaceutically acceptable salt thereof." should read -- The compound according to claim 1, wherein the peptide bond between $A^1$ and $A^2$ is a pseudopeptide bond; or a pharmaceutically acceptable salt thereof. --

SEQUENCE LISTING

<160> NUMBER OF SEQ ID NOS: 96

<210> SEQ ID NO 1
<211> LENGTH: 42
<212> TYPE: PRT
<213> ORGANISM: Homo sapiens

<400> SEQUENCE: 1

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 2
<211> LENGTH: 30
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: AMIDATION

<400> SEQUENCE: 2

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 3
<211> LENGTH: 42
<212> TYPE: PRT
<213> ORGANISM: Artificial sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = 1-amino-1-cyclopentanecarboxylic acid

<400> SEQUENCE: 3

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 4
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = 3-(4-hydroxyphenyl)propionic acid (4Hppa)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE -continued

```
<222> LOCATION: (7)..(7)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MOD_RES
<222> LOCATION: (30)..(30)
<223> OTHER INFORMATION: AMIDATION

<400> SEQUENCE: 4

Xaa Xaa Glu Gly Thr Phe Xaa Ser Asp Tyr Ser Ile Ala Xaa Asp Lys
1               5                   10                  15

Ile His Gln Gln Asp Phe Val Asn Trp Leu Leu Ala Gln Lys
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = 3-(4-hydroxyphenyl)propionic acid (4Hppa)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = alpha-aminoisobutyric acid (Aib)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MOD_RES
<222> LOCATION: (30)..(30)
<223> OTHER INFORMATION: AMIDATION

<400> SEQUENCE: 5

Xaa Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = 3-(4-hydroxyphenyl)propionic acid (4Hppa)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclopentanecarboxylic acid
      (A5c)
<220> FEATURE:
```

```
<221> NAME/KEY: MOD_RES
<222> LOCATION: (30)..(30)
<223> OTHER INFORMATION: AMIDATION

<400> SEQUENCE: 6

Xaa Xaa Glu Gly Thr Phe Xaa Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = 3-(4-hydroxyphenyl)propionic acid (4Hppa)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = alpha-aminoisobutyric acid (Aib)
<220> FEATURE:
<221> NAME/KEY: MOD_RES
<222> LOCATION: (30)..(30)
<223> OTHER INFORMATION: AMIDATION

<400> SEQUENCE: 7

Xaa Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = 3-(4-hydroxyphenyl)propionic acid (4Hppa)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MOD_RES
<222> LOCATION: (30)..(30)
<223> OTHER INFORMATION: AMIDATION

<400> SEQUENCE: 8

Xaa Xaa Glu Gly Thr Phe Ile Ser Asp Tyr Ser Ile Ala Xaa Asp Lys
1               5                   10                  15

Ile His Gln Gln Asp Phe Val Asn Trp Leu Leu Ala Gln Lys
            20                  25                  30
```

<210> SEQ ID NO 9
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = 3-(4-hydroxyphenyl)propionic acid (4Hppa)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (30)..(30)
<223> OTHER INFORMATION: AMIDATION

<400> SEQUENCE: 9

Xaa Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 10
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = 3-(4-hydroxyphenyl)propionic acid (4Hppa)
<220> FEATURE:
<221> NAME/KEY: MISC_FEATURE
<222> LOCATION: (3)..(3)
<223> OTHER INFORMATION: Xaa = 4-hydroxyproline (4Hyp)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)

<400> SEQUENCE: 10

Xaa Ala Xaa Gly Thr Phe Xaa Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
            35                  40

<210> SEQ ID NO 11
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = 3-(4-hydroxyphenyl)propionic acid (4Hppa)
<220> FEATURE:
<221> NAME/KEY: MISC_FEATURE
<222> LOCATION: (3)..(3)
<223> OTHER INFORMATION: Xaa = homoproline (hPro)
<220> FEATURE:
<221> NAME/KEY: MISC_FEATURE

```
<222> LOCATION: (7)..(7)
<223> OTHER INFORMATION: Xaa = 1-amino-1-cyclohexanecarboxylic acid
      (A6c)

<400> SEQUENCE: 11

Xaa Ala Xaa Gly Thr Phe Xaa Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
            35                  40

<210> SEQ ID NO 12
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = 3-(4-hydroxyphenyl)propionic acid (4Hppa)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (3)..(3)
<223> OTHER INFORMATION: Xaa = homoproline (hPro)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MOD_RES
<222> LOCATION: (30)..(30)
<223> OTHER INFORMATION: AMIDATION

<400> SEQUENCE: 12

Xaa Xaa Xaa Gly Thr Phe Ile Ser Asp Tyr Ser Ile Ala Xaa Asp Lys
1               5                   10                  15

Ile His Gln Gln Asp Phe Val Asn Trp Leu Leu Ala Gln Lys
            20                  25                  30

<210> SEQ ID NO 13
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (13)..(13)
<223> OTHER INFORMATION: Xaa = alpha-aminoisobutyric acid (Aib)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 13

His Xaa Glu Gly Thr Phe Ile Ser Asp Tyr Ser Ile Xaa Xaa Asp Lys
1               5                   10                  15

Ile His Gln Gln Asp Phe Val Asn Trp Leu Leu Ala Gln Lys Gly Lys
```

Lys Asn Asp Trp Lys His Asn Ile Thr Gln
            35                  40

<210> SEQ ID NO 14
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: brominated at positions 3 and 5
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (13)..(13)
<223> OTHER INFORMATION: Xaa = alpha-aminoisobutyric acid (Aib)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 14

Tyr Xaa Glu Gly Thr Phe Ile Ser Asp Tyr Ser Ile Xaa Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
            35                  40

<210> SEQ ID NO 15
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 15

His Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
            35                  40

<210> SEQ ID NO 16
<211> LENGTH: 42
<212> TYPE: PRT
<213> ORGANISM: Artificial Sequence

```
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: brominated at positions 3 and 5
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 16

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 17
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: chlorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 17

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 18
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
```

```
<222> LOCATION: (1)..(1)
<223> OTHER INFORMATION: brominated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 18

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 19
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: iodinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 19

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 20
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: iodinated at positions 3 and 5
<220> FEATURE:
<221> NAME/KEY: MISC_FEATURE
<222> LOCATION: (2)..(2)
```

```
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 20

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 21
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: amidated at position 4
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 21

Phe Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 22
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = homotyrosine (hTyr)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
```

```
              (A5c)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 22

Xaa Xaa Glu Gly Thr Phe Ile Ser Asp Tyr Xaa Ile Ala Xaa Asp Lys
1               5                  10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 23
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = 4-Cl-phenylalanine (Cpa)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 23

Xaa Xaa Glu Gly Thr Phe Ile Ser Asp Tyr Xaa Ile Ala Xaa Asp Lys
1               5                  10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 24
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: modified with aminomethyl group at postion 4
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)
```

-continued

<400> SEQUENCE: 24

Phe Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 25
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: fluorinated at positions 3, 4 and 5
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 25

Phe Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 26
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: fluorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 26

Phe Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 27
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: fluorinated at positions 3 and 4
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 27

Phe Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 28
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: fluorinated at positions 3 and 5
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 28

Phe Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln

<210> SEQ ID NO 29
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: hydroxylated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 29

Phe Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln
        35                  40

<210> SEQ ID NO 30
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: hydroxylated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 30

Tyr Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln
        35                  40

-continued

```
<210> SEQ ID NO 31
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: O-methyl at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 31

Tyr Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln
            35                  40

<210> SEQ ID NO 32
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 32

Tyr Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln
            35                  40

<210> SEQ ID NO 33
<211> LENGTH: 42
<212> TYPE: PRT
```

```
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: methylated at positions 2 and 6
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 33

Tyr Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln
        35                  40

<210> SEQ ID NO 34
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: methylation
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 34

Tyr Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln
        35                  40

<210> SEQ ID NO 35
<211> LENGTH: 42
<212> TYPE: PRT
<213> ORGANISM: Artificial Sequence
<220> FEATURE:
<223> OTHER INFORMATION: Synthetic analog of glucose-dependent
``` insulinotropic polypeptide (GIP)
<220> FEATURE:
<221> NAME/KEY: MOD_RES
<222> LOCATION: (1)..(1)
<223> OTHER INFORMATION: fluorinated at position 4
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
    (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
    (A5c)

<400> SEQUENCE: 35

Phe Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln
        35                  40

<210> SEQ ID NO 36
<211> LENGTH: 42
<212> TYPE: PRT
<213> ORGANISM: Artificial Sequence
<220> FEATURE:
<223> OTHER INFORMATION: Synthetic analog of glucose-dependent
    insulinotropic polypeptide (GIP)
<220> FEATURE:
<221> NAME/KEY: MISC_FEATURE
<222> LOCATION: (1)..(1)
<223> OTHER INFORMATION: Xaa = beta-(4-pyridinyl)alanine (4Pal)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
    (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
    (A5c)

<400> SEQUENCE: 36

Xaa Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln
        35                  40

<210> SEQ ID NO 37
<211> LENGTH: 42
<212> TYPE: PRT
<213> ORGANISM: Artificial Sequence
<220> FEATURE:
<223> OTHER INFORMATION: Synthetic analog of glucose-dependent
    insulinotropic polypeptide (GIP)
<220> FEATURE:
<221> NAME/KEY: MISC_FEATURE

```
<222> LOCATION: (1)..(1)
<223> OTHER INFORMATION: Xaa = beta-(3-pyridinyl)alanine (3Pal)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 37

Xaa Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln
        35                  40

<210> SEQ ID NO 38
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = beta-(4-thiazolyl)alanine (Taz)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 38

Xaa Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln
        35                  40

<210> SEQ ID NO 39
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: modified with NO2 group at position 3
<220> FEATURE:
```

<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 39

Tyr Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln
        35                  40

<210> SEQ ID NO 40
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = beta-(3-thienyl)alanine (3Thi)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 40

Xaa Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln
        35                  40

<210> SEQ ID NO 41
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: modified with CN at position 4
<220> FEATURE:
<221> NAME/KEY: MISC_FEATURE
<222> LOCATION: (2)..(2)
<223> OTHER INFORMATION: Xaa = alpha-aminoisobutyric acid (Aib)

```
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 41

Phe Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln
        35                  40

<210> SEQ ID NO 42
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: fluorinated at position 3
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (40)..(40)
<223> OTHER INFORMATION: Xaa = 1-amino-1-cyclopentanecarboxylic acid
      (A5c)

<400> SEQUENCE: 42

Tyr Gly Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Xaa Thr Gln
        35                  40

<210> SEQ ID NO 43
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(2)
<223> OTHER INFORMATION: pseudopeptide bond
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)
```

<400> SEQUENCE: 43

Tyr Gly Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln
        35                  40

<210> SEQ ID NO 44
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: fluorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 44

Phe Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln
        35                  40

<210> SEQ ID NO 45
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: chlorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 45

Phe Xaa Glu Gly Thr Phe Ile Ser Asp Tyr Xaa Ile Ala Met Asp Lys

```
                1               5                  10                  15
Ile His Gln Gln Asp Phe Val Asn Trp Leu Leu Ala Gln Lys Gly Lys
                    20                  25                  30

Lys Asn Asp Trp Lys His Asn Ile Xaa Gln
            35                  40
```

<210> SEQ ID NO 46
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: brominated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 46

```
Phe Xaa Glu Gly Thr Phe Ile Ser Asp Tyr Xaa Ile Ala Met Asp Lys
1               5                  10                  15

Ile His Gln Gln Asp Phe Val Asn Trp Leu Leu Ala Gln Lys Gly Lys
                    20                  25                  30

Lys Asn Asp Trp Lys His Asn Ile Xaa Gln
            35                  40
```

<210> SEQ ID NO 47
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: chlorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 47

```
Tyr Xaa Glu Gly Thr Phe Ile Ser Asp Tyr Xaa Ile Ala Met Asp Lys
1               5                  10                  15

Ile His Gln Gln Asp Phe Val Asn Trp Leu Leu Ala Gln Lys Gly Lys
```

Lys Asn Asp Trp Lys His Asn Ile Xaa Gln
        35                  40

<210> SEQ ID NO 48
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: brominated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 48

Tyr Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln
        35                  40

<210> SEQ ID NO 49
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = beta-tyrosine (-Tyr)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 49

Xaa Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln

<210> SEQ ID NO 50
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: fluorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 50

Tyr Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln
        35                  40

<210> SEQ ID NO 51
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: fluorinated at position 2
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 51

Tyr Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln
        35                  40

```
<210> SEQ ID NO 52
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = a-methyl-tyrosine
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 52

Xaa Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln
        35                  40

<210> SEQ ID NO 53
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: AMIDATION at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 53

Tyr Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln
        35                  40

<210> SEQ ID NO 54
<211> LENGTH: 42
<212> TYPE: PRT
```

```
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = beta-(2-pyridinyl)alanine (2Pal)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 54

Xaa Xaa Glu Gly Thr Phe Ile Ser Asp Tyr Xaa Ile Ala Met Asp Lys
1               5                  10                  15

Ile His Gln Gln Asp Phe Val Asn Trp Leu Leu Ala Gln Lys Gly Lys
            20                  25                  30

Lys Asn Asp Trp Lys His Asn Ile Xaa Gln
        35                  40

<210> SEQ ID NO 55
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: modified with (HO-CH2) at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 55

Tyr Xaa Glu Gly Thr Phe Ile Ser Asp Tyr Xaa Ile Ala Met Asp Lys
1               5                  10                  15

Ile His Gln Gln Asp Phe Val Asn Trp Leu Leu Ala Gln Lys Gly Lys
            20                  25                  30

Lys Asn Asp Trp Lys His Asn Ile Xaa Gln
        35                  40

<210> SEQ ID NO 56
<211> LENGTH: 43
<212> TYPE: PRT
<213> ORGANISM: Artificial Sequence
<220> FEATURE:
<223> OTHER INFORMATION: Synthetic analog of glucose-dependent
```

```
        insulinotropic polypeptide (GIP)
<220> FEATURE:
<221> NAME/KEY: MOD_RES
<222> LOCATION: (1)..(1)
<223> OTHER INFORMATION: methylated at positions 2 and 6
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
        (A5c)

<400> SEQUENCE: 56

Tyr Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln His
        35                  40

<210> SEQ ID NO 57
<211> LENGTH: 43
<212> TYPE: PRT
<213> ORGANISM: Artificial Sequence
<220> FEATURE:
<223> OTHER INFORMATION: Synthetic analog of glucose-dependent
        insulinotropic polypeptide (GIP)
<220> FEATURE:
<221> NAME/KEY: MOD_RES
<222> LOCATION: (1)..(1)
<223> OTHER INFORMATION: methylated at positions 2 and 6
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
        (A5c)
<220> FEATURE:
<221> NAME/KEY: MISC_FEATURE
<222> LOCATION: (14)..(14)
<223> OTHER INFORMATION: Xaa = 1-amino-1-cyclopentanecarboxylic acid
        (A5c)

<400> SEQUENCE: 57

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln His
        35                  40

<210> SEQ ID NO 58
<211> LENGTH: 43
<212> TYPE: PRT
<213> ORGANISM: Artificial Sequence
<220> FEATURE:
<223> OTHER INFORMATION: Synthetic analog of glucose-dependent
        insulinotropic polypeptide (GIP)
<220> FEATURE:
<221> NAME/KEY: MOD_RES
<222> LOCATION: (1)..(1)
<223> OTHER INFORMATION: methylated at positions 2 and 6
<220> FEATURE:
<221> NAME/KEY: MISC_FEATURE
<222> LOCATION: (2)..(2)
```

```
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 58

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln His
        35                  40

<210> SEQ ID NO 59
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: fluorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 59

Phe Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln
        35                  40

<210> SEQ ID NO 60
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: fluorinated at position 3
<220> FEATURE:
<221> NAME/KEY: MISC_FEATURE
```

```
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 60

Phe Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln His
        35                  40

<210> SEQ ID NO 61
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: fluorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 61

Phe Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln His
        35                  40

<210> SEQ ID NO 62
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: fluorinated at position 3
<220> FEATURE:
```

-continued

```
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 62

Phe Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln His
        35                  40

<210> SEQ ID NO 63
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: chlorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = 1-amino-1-cyclopentanecarboxylic acid
      (A5c)

<400> SEQUENCE: 63

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln His
        35                  40

<210> SEQ ID NO 64
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
```

<223> OTHER INFORMATION: chlorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 64

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln His
        35                  40

<210> SEQ ID NO 65
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: chlorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MISC_FEATURE
<222> LOCATION: (43)..(43)
<223> OTHER INFORMATION: Xaa = ornithine (Orn)
<220> FEATURE:
<221> NAME/KEY: MOD_RES
<222> LOCATION: (43)..(43)
<223> OTHER INFORMATION: modified with (N-C(O)-(CH2)10-CH3)

<400> SEQUENCE: 65

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Xaa
        35                  40

<210> SEQ ID NO 66
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)

```
<220> FEATURE:
<221> NAME/KEY: MOD_RES
<222> LOCATION: (1)..(1)
<223> OTHER INFORMATION: chlorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MOD_RES
<222> LOCATION: (43)..(43)
<223> OTHER INFORMATION: modified with succinimide-N-(CH2)11-CH3

<400> SEQUENCE: 66

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Cys
            35                  40

<210> SEQ ID NO 67
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: brominated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 67

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln His
            35                  40

<210> SEQ ID NO 68
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
```

```
<221> NAME/KEY: MOD_RES
<222> LOCATION: (1)..(1)
<223> OTHER INFORMATION: brominated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = 1-amino-1-cyclopentanecarboxylic acid
      (A5c)

<400> SEQUENCE: 68

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln His
        35                  40

<210> SEQ ID NO 69
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = 3-O-methyl-tyrosine
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)

<400> SEQUENCE: 69

Xaa Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln His
        35                  40

<210> SEQ ID NO 70
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = 3-O-methyl-tyrosine
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
```

```
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = 1-amino-1-cyclopentanecarboxylic acid
      (A5c)

<400> SEQUENCE: 70

Xaa Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln His
        35                  40

<210> SEQ ID NO 71
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = 3-O-methyl-tyrosine
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 71

Xaa Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln His
        35                  40

<210> SEQ ID NO 72
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = 4-trifluoromethyl-phenylalanine
      (4CF3-Phe)
<220> FEATURE:
<221> NAME/KEY: MISC_FEATURE
```

```
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)

<400> SEQUENCE: 72

Xaa Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln His
        35                  40

<210> SEQ ID NO 73
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = 7-Hydroxy-1,2,3,4-tetrahydroisoquinoline-
      3-carboxylic acid (7HO-Tic)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)

<400> SEQUENCE: 73

Xaa Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln His
        35                  40

<210> SEQ ID NO 74
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: methylated at position 4
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)

<400> SEQUENCE: 74

Phe Xaa Glu Gly Thr Phe Ile Ser Asp Tyr Xaa Ile Ala Met Asp Lys
1               5                   10                  15
```

Ile His Gln Gln Asp Phe Val Asn Trp Leu Leu Ala Gln Lys Gly Lys
            20                  25                  30

Lys Asn Asp Trp Lys His Asn Ile Thr Gln His
            35                  40

<210> SEQ ID NO 75
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: modified with a cyano group (CN) at position 4
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)

<400> SEQUENCE: 75

Phe Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln His
            35                  40

<210> SEQ ID NO 76
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = homotyrosine (hTyr)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)

<400> SEQUENCE: 76

Xaa Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln His
            35                  40

<210> SEQ ID NO 77
<211> LENGTH: 43
<212> TYPE: PRT
<213> ORGANISM: Artificial Sequence
<220> FEATURE:

```
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: chlorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MOD_RES
<222> LOCATION: (43)..(43)
<223> OTHER INFORMATION: modified with (N-C(O)-(CH2)10-CH3)

<400> SEQUENCE: 77

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Lys
        35                  40

<210> SEQ ID NO 78
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: chlorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = 1-amino-1-cyclopentanecarboxylic acid
      (A5c)
<220> FEATURE:
<221> NAME/KEY: MOD_RES
<222> LOCATION: (43)..(43)
<223> OTHER INFORMATION: modified with (N-C(O)-(CH2)10-CH3)

<400> SEQUENCE: 78

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Lys
        35                  40

<210> SEQ ID NO 79
```

-continued

```
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: chlorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 79

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Cys
        35                  40

<210> SEQ ID NO 80
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: chlorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MOD_RES
<222> LOCATION: (43)..(43)
<223> OTHER INFORMATION: AMIDATION
<220> FEATURE:
<221> NAME/KEY: MOD_RES
<222> LOCATION: (43)..(43)
<223> OTHER INFORMATION: modified with succinimide-N-20K PEG

<400> SEQUENCE: 80

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Cys
        35                  40
```

<210> SEQ ID NO 81
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: chlorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MOD_RES
<222> LOCATION: (43)..(43)
<223> OTHER INFORMATION: AMIDATION
<220> FEATURE:
<221> NAME/KEY: MOD_RES
<222> LOCATION: (43)..(43)
<223> OTHER INFORMATION: modified with succinimide-N-30K PEG

<400> SEQUENCE: 81

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Cys
        35                  40

<210> SEQ ID NO 82
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: chlorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MOD_RES
<222> LOCATION: (43)..(43)
<223> OTHER INFORMATION: AMIDATION
<220> FEATURE:
<221> NAME/KEY: MOD_RES
<222> LOCATION: (43)..(43)
<223> OTHER INFORMATION: modified with succinimide-N-60K PEG

<400> SEQUENCE: 82

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Cys
        35                  40

<210> SEQ ID NO 83
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: chlorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = 1-amino-1-cyclopentanecarboxylic acid
      (A5c)
<220> FEATURE:
<221> NAME/KEY: MOD_RES
<222> LOCATION: (43)..(43)
<223> OTHER INFORMATION: AMIDATION
<220> FEATURE:
<221> NAME/KEY: MOD_RES
<222> LOCATION: (43)..(43)
<223> OTHER INFORMATION: modified with succinimide-N-60K PEG

<400> SEQUENCE: 83

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Cys
        35                  40

<210> SEQ ID NO 84
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: chlorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)

```
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MOD_RES
<222> LOCATION: (43)..(43)
<223> OTHER INFORMATION: AMIDATION
<220> FEATURE:
<221> NAME/KEY: MOD_RES
<222> LOCATION: (43)..(43)
<223> OTHER INFORMATION: modified with succinimide-N-(CH2)2-C(O)NH-
      (CH2)3-20K PEG

<400> SEQUENCE: 84

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Cys
        35                  40

<210> SEQ ID NO 85
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: chlorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MOD_RES
<222> LOCATION: (32)..(32)
<223> OTHER INFORMATION: modified with succinimide-N-(CH2)2-C(O)NH-
      (CH2)3-20K PEG
<220> FEATURE:
<221> NAME/KEY: MOD_RES
<222> LOCATION: (42)..(42)
<223> OTHER INFORMATION: AMIDATION

<400> SEQUENCE: 85

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Cys
            20                  25                  30

Lys Asn Asp Trp Lys His Asn Ile Thr Gln
        35                  40

<210> SEQ ID NO 86
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
```

```
<220> FEATURE:
<221> NAME/KEY: MOD_RES
<222> LOCATION: (1)..(1)
<223> OTHER INFORMATION: chlorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MOD_RES
<222> LOCATION: (33)..(33)
<223> OTHER INFORMATION: modified with succinimide-N-(CH2)2-C(O)NH-
      (CH2)3-20K PEG
<220> FEATURE:
<221> NAME/KEY: MOD_RES
<222> LOCATION: (42)..(42)
<223> OTHER INFORMATION: AMIDATION

<400> SEQUENCE: 86

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Cys Asn Asp Trp Lys His Asn Ile Thr Gln
        35                  40

<210> SEQ ID NO 87
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: chlorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MOD_RES
<222> LOCATION: (43)..(43)
<223> OTHER INFORMATION: AMIDATION
<220> FEATURE:
<221> NAME/KEY: MOD_RES
<222> LOCATION: (43)..(43)
<223> OTHER INFORMATION: modified with succinimide-N-(CH2)2-C(O)NH-
      (CH2)3-O-CH2-CH(20K PEG)-CH2-20K PEG

<400> SEQUENCE: 87

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
```

-continued

```
                20                  25                  30
Lys Asn Asp Trp Lys His Asn Ile Thr Gln Cys
        35                  40

<210> SEQ ID NO 88
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: chlorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MOD_RES
<222> LOCATION: (32)..(32)
<223> OTHER INFORMATION: modified with succinimide-N-(CH2)2-C(O)NH-
      (CH2)3-O-CH2-CH(20K PEG)-CH2-20K PEG
<220> FEATURE:
<221> NAME/KEY: MOD_RES
<222> LOCATION: (42)..(42)
<223> OTHER INFORMATION: AMIDATION

<400> SEQUENCE: 88

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Cys
            20                  25                  30

Lys Asn Asp Trp Lys His Asn Ile Thr Gln
        35                  40

<210> SEQ ID NO 89
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: chlorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MOD_RES
<222> LOCATION: (33)..(33)
```

```
<223> OTHER INFORMATION: modified with succinimide-N-(CH2)2-C(O)NH-
      (CH2)3-O-CH2-CH(20K PEG)-CH2-20K PEG
<220> FEATURE:
<221> NAME/KEY: MOD_RES
<222> LOCATION: (42)..(42)
<223> OTHER INFORMATION: AMIDATION

<400> SEQUENCE: 89

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Cys Asn Asp Trp Lys His Asn Ile Thr Gln
        35                  40

<210> SEQ ID NO 90
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: chlorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = 1-amino-1-cyclopentanecarboxylic acid
      (A5c)
<220> FEATURE:
<221> NAME/KEY: MOD_RES
<222> LOCATION: (43)..(43)
<223> OTHER INFORMATION: AMIDATION
<220> FEATURE:
<221> NAME/KEY: MOD_RES
<222> LOCATION: (43)..(43)
<223> OTHER INFORMATION: modified with succinimide-N-(CH2)2-C(O)NH-
      (CH2)3-20K PEG

<400> SEQUENCE: 90

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Cys
        35                  40

<210> SEQ ID NO 91
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: chlorinated at position 3
<220> FEATURE:
<221> NAME/KEY: MISC_FEATURE
```

```
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = 1-amino-1-cyclopentanecarboxylic acid
      (A5c)
<220> FEATURE:
<221> NAME/KEY: MOD_RES
<222> LOCATION: (32)..(32)
<223> OTHER INFORMATION: modified with succinimide-N-(CH2)2-C(O)NH-
      (CH2)3-20K PEG
<220> FEATURE:
<221> NAME/KEY: MOD_RES
<222> LOCATION: (42)..(42)
<223> OTHER INFORMATION: AMIDATION

<400> SEQUENCE: 91

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Cys
            20                  25                  30

Lys Asn Asp Trp Lys His Asn Ile Thr Gln
        35                  40

<210> SEQ ID NO 92
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: chlorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = 1-amino-1-cyclopentanecarboxylic acid
      (A5c)
<220> FEATURE:
<221> NAME/KEY: MOD_RES
<222> LOCATION: (33)..(33)
<223> OTHER INFORMATION: modified with succinimide-N-(CH2)2-C(O)NH-
      (CH2)3-20K PEG
<220> FEATURE:
<221> NAME/KEY: MOD_RES
<222> LOCATION: (42)..(42)
<223> OTHER INFORMATION: AMIDATION

<400> SEQUENCE: 92

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Cys Asn Asp Trp Lys His Asn Ile Thr Gln
        35                  40
```

<210> SEQ ID NO 93
<211> LENGTH: 43
<212> TYPE: PRT
<213> ORGANISM: Artificial Sequence
<220> FEATURE:
<223> OTHER INFORMATION: Synthetic analog of glucose-dependent
    insulinotropic polypeptide (GIP)
<220> FEATURE:
<221> NAME/KEY: MOD_RES
<222> LOCATION: (1)..(1)
<223> OTHER INFORMATION: chlorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
    (A5c)
<220> FEATURE:
<221> NAME/KEY: MISC_FEATURE
<222> LOCATION: (14)..(14)
<223> OTHER INFORMATION: Xaa = 1-amino-1-cyclopentanecarboxylic acid
    (A5c)
<220> FEATURE:
<221> NAME/KEY: MOD_RES
<222> LOCATION: (43)..(43)
<223> OTHER INFORMATION: AMIDATION
<220> FEATURE:
<221> NAME/KEY: MOD_RES
<222> LOCATION: (43)..(43)
<223> OTHER INFORMATION: modified with succinimide-N-(CH2)2-C(O)NH-
    (CH2)3-O-CH2-CH(20K PEG)-CH2-20K PEG

<400> SEQUENCE: 93

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Cys
        35                  40

<210> SEQ ID NO 94
<211> LENGTH: 42
<212> TYPE: PRT
<213> ORGANISM: Artificial Sequence
<220> FEATURE:
<223> OTHER INFORMATION: Synthetic analog of glucose-dependent
    insulinotropic polypeptide (GIP)
<220> FEATURE:
<221> NAME/KEY: MOD_RES
<222> LOCATION: (1)..(1)
<223> OTHER INFORMATION: chlorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
    (A5c)
<220> FEATURE:
<221> NAME/KEY: MISC_FEATURE
<222> LOCATION: (14)..(14)
<223> OTHER INFORMATION: Xaa = 1-amino-1-cyclopentanecarboxylic acid
    (A5c)
<220> FEATURE:
<221> NAME/KEY: MOD_RES
<222> LOCATION: (32)..(32)
<223> OTHER INFORMATION: modified with succinimide-N-(CH2)2-C(O)NH-
    (CH2)3-O-CH2-CH(20K PEG)-CH2-20K PEG

```
<220> FEATURE:
<221> NAME/KEY: MOD_RES
<222> LOCATION: (42)..(42)
<223> OTHER INFORMATION: AMIDATION

<400> SEQUENCE: 94

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Cys
            20                  25                  30

Lys Asn Asp Trp Lys His Asn Ile Thr Gln
        35                  40

<210> SEQ ID NO 95
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MOD_RES
<222> LOCATION: (1)..(1)
<223> OTHER INFORMATION: chlorinated at position 3
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = 1-amino-1-cyclopentanecarboxylic acid
      (A5c)
<220> FEATURE:
<221> NAME/KEY: MOD_RES
<222> LOCATION: (33)..(33)
<223> OTHER INFORMATION: modified with succinimide-N-(CH2)2-C(O)NH-
      (CH2)3-O-CH2-CH(20K PEG)-CH2-20K PEG
<220> FEATURE:
<221> NAME/KEY: MOD_RES
<222> LOCATION: (42)..(42)
<223> OTHER INFORMATION: AMIDATION

<400> SEQUENCE: 95

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Cys Asn Asp Trp Lys His Asn Ile Thr Gln
        35                  40

<210> SEQ ID NO 96
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = 3-(4-hydroxyphenyl)propionic acid (4Hppa)
<220> FEATURE:
<221> NAME/KEY: MISC_FEATURE
<222> LOCATION: (2)..(2)
<223> OTHER INFORMATION: Xaa = alpha-aminoisobutyric acid (Aib)
```

```
<220> FEATURE:
<221> NAME/KEY: MISC_FEATURE
<222> LOCATION: (7)..(7)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 96

Xaa Xaa Glu Gly Thr Phe Xaa Ser Asp Tyr Ser Ile Ala Xaa Asp Lys
1               5                   10                  15

Ile His Gln Gln Asp Phe Val Asn Trp Leu Leu Ala Gln Lys
            20                  25                  30
```